(12) United States Patent
Lewis et al.

(10) Patent No.: US 7,495,120 B2
(45) Date of Patent: Feb. 24, 2009

(54) NANOSIZED COPPER CATALYST PRECURSORS FOR THE DIRECT SYNTHESIS OF TRIALKOXYSILANES

(75) Inventors: Kenrick M. Lewis, Rego Park, NY (US); Regina Nelson Eng, Pike Road, AL (US); Sabrina R. Cromer, Mount Vernon, NY (US); Abellard T. Mereigh, Yonkers, NY (US); Chi-Lin O'Young, Poughkeepsie, NY (US)

(73) Assignee: Momentive Performance Materials Inc., Albany, NY (US)

(*) Notice: Subject to any disclaimer, the term of this patent is extended or adjusted under 35 U.S.C. 154(b) by 0 days.

(21) Appl. No.: 11/975,787

(22) Filed: Dec. 17, 2007

(65) Prior Publication Data

US 2008/0081923 A1    Apr. 3, 2008

Related U.S. Application Data

(62) Division of application No. 09/974,092, filed on Oct. 9, 2001, now Pat. No. 7,339,068.

(60) Provisional application No. 60/265,154, filed on Jan. 31, 2001.

(51) Int. Cl.
   *C07F 7/04* (2006.01)
(52) U.S. Cl. .............. 556/465; 556/400; 556/466; 556/470
(58) Field of Classification Search ............. 556/400, 556/465, 466, 470
   See application file for complete search history.

(56) References Cited

U.S. PATENT DOCUMENTS

| | | | |
|---|---|---|---|
| 2,380,995 A | 8/1945 | Rochow et al. | |
| 3,428,530 A | 2/1969 | Fauche et al. | |
| 3,505,379 A | 4/1970 | Bonitz | |
| 3,641,077 A | 2/1972 | Rochow | |
| 3,775,457 A | 11/1973 | Muraoka et al. | |
| 4,450,282 A | 5/1984 | Ritzer et al. | |
| 4,727,173 A | 2/1988 | Medicino | |
| 4,730,074 A * | 3/1988 | Lewis et al. | 556/470 |
| 4,761,492 A | 8/1988 | Childress et al. | |
| 4,762,940 A | 8/1988 | Haim et al. | |
| 4,864,044 A | 9/1989 | Lewis et al. | |
| 4,946,980 A | 8/1990 | Haim et al. | |
| 4,999,446 A | 3/1991 | Moody et al. | |
| 5,166,384 A | 11/1992 | Bailey et al. | |
| 5,362,897 A | 11/1994 | Harada et al. | |
| 5,527,937 A | 6/1996 | Standke et al. | |
| 5,728,858 A | 3/1998 | Lewis et al. | |
| 5,783,720 A * | 7/1998 | Mendicino et al. | 556/470 |
| 5,880,307 A | 3/1999 | Daugherty et al. | |
| 5,998,548 A | 12/1999 | Brennenstuhl et al. | |
| 6,001,948 A | 12/1999 | Scheim et al. | |
| 6,013,718 A | 1/2000 | Cabioch et al. | |
| 6,018,011 A | 1/2000 | Scheim et al. | |
| 6,020,068 A | 2/2000 | Kawazura et al. | |
| 6,020,449 A | 2/2000 | Scheim | |
| 6,057,469 A | 5/2000 | Margaria et al. | |
| 6,090,965 A | 7/2000 | Lewis et al. | |
| 6,090,966 A | 7/2000 | Nakanishi et al. | |
| 6,140,393 A | 10/2000 | Bomal et al. | |
| 6,258,970 B1 | 7/2001 | Ward, III et al. | |
| 6,288,258 B1 | 9/2001 | Aramata et al. | |
| 6,339,167 B2 | 1/2002 | Aramata et al. | |
| 6,380,414 B2 | 4/2002 | Brand | |
| 6,407,276 B1 | 6/2002 | Lewis et al. | |
| 6,410,771 B1 | 6/2002 | Brand | |
| 6,423,860 B1 | 7/2002 | Lewis et al. | |
| 6,506,923 B2 | 1/2003 | Inukai et al. | |
| 6,528,674 B1 | 3/2003 | Lewis et al. | |
| 6,686,312 B1 | 2/2004 | Aramata et al. | |
| 2002/0010354 A1 | 1/2002 | Brand et al. | |
| 2003/0013902 A1 | 1/2003 | Brand et al. | |

(Continued)

FOREIGN PATENT DOCUMENTS

DE        5348        4/1878

(Continued)

OTHER PUBLICATIONS

U.S. Appl. No. 09/974,092, filed Oct. 2001, Lewis.

(Continued)

*Primary Examiner*—Shailendra Kumar
(74) *Attorney, Agent, or Firm*—Dominick G. Vicari

(57) ABSTRACT

The present invention provides a process for using nanosized copper, nanosized copper oxides, nanosized copper chlorides, other nanosized copper salts, and mixtures thereof, as sources of catalytic copper in the Direct Synthesis of trialkoxysilanes of the formula $HSi(OR)_3$ wherein R is an alkyl group containing from 1 to 6 carbon atoms inclusive. The nanosized copper, nanosized copper oxides, nanosized copper chlorides, other nanosized copper salts, and their mixtures of this invention have average particle sizes that are in the range from about 0.1 to about 600 nanometers, preferably from about 0.1 to about 500 nanometers, and most preferably from about 0.1 to about 100 nanometers. Nanosized sources of catalytic copper afford high dispersion of catalytic sites on silicon and contribute to high reaction rates, high selectivity and high silicon conversion. The nanosized copper catalyst precursors of the invention permit the use of substantially reduced levels of copper compared to conventional practice.

12 Claims, 6 Drawing Sheets

U.S. PATENT DOCUMENTS

| | | |
|---|---|---|
| 2003/0065204 A1 | 4/2003 | Lewis et al. |
| 2008/0103323 A1 | 5/2008 | Cromer |

FOREIGN PATENT DOCUMENTS

| | | |
|---|---|---|
| DE | 887 343 | 8/1953 |
| DE | 920 187 | 11/1954 |
| DE | 1 079 607 | 4/1960 |
| DE | 10 88 051 | 9/1960 |
| DE | 11 00 006 | 2/1961 |
| DE | 1 132 901 | 7/1962 |
| DE | 1 161 430 | 1/1964 |
| EP | 784072 | 12/1986 |
| EP | 0 784 056 | 7/1997 |
| EP | 784072 | 7/1997 |
| EP | 0835876 A2 | 4/1998 |
| EP | 1157993 A2 | 11/2001 |
| EP | 1172366 A2 | 1/2002 |
| JP | 55-2641 | 1/1980 |
| JP | 55-28929 | 3/1980 |
| JP | 55-76891 | 6/1980 |
| JP | 57-108094 | 6/1982 |
| JP | 62-96433 | 4/1987 |
| JP | 10-182660 | 6/1998 |
| JP | 10-182660 | 7/1998 |
| JP | 11-21288 | 1/1999 |
| WO | 85/05047 | 11/1985 |
| WO | 00/63217 | 10/2000 |
| WO | 01/47937 A1 | 7/2001 |
| WO | 02/060623 | 8/2002 |
| WO | 02/060909 | 8/2002 |

OTHER PUBLICATIONS

U.S. Appl. No. 60/265,154, filed Jan. 2001, Lewis.
Newton, W.E. and Rochow, E.G., The Direct Synthesis of Organic Derivatives of Silicon Using Nonhalogenated Organic Compounds, pp. 1071-1075, vol. 9, No. 5, May 1970.
Suzuki et al., Bulletin of the Chemical Society of Japan, vol. 64 (1991) pp. 3445-3447.
Brunauer, Stephen, Emmett, P.H. and Teller, Edward, Absorption of Gases in Multimolecular Layers, (1938), pp. 309-319, vol. 60, U.S.A.
CA:112:38601 abs of Kecheng Xiangjiao Gongye by Nan, C. 12(5) pp. 293-296 1989.
Stantke, P. & Scmitz, J., Influence of Tin—Addition To A Copper Catalyst On Direct Synthesis, Silicon for the Chemical Industry (2000), pp. 227-233, Trodheim, Norway.
Stantke, P., New Copper Oxide Base Catalyst for the Rochow Synthesis with Low Bet (1998), 227-238, Trodheim, Norway.
Bonitz, E., Reactions of Elementary Silicon, Angew. Chem. Internat. Edit. (1966), pp. 462-469, vol. 5, No. 5, Germany.
U.S. Appl. No. US 2002/0010354 a1; Published Jan. 24, 2002; English Equivalent for EP 1157993 A2.
Zapletal, V. Jedlicka, J. & Ruzicka, V., Die Thermische Zersetzung Einiger Metallformate, Collection Czechslov, Chem. Commun. (1957), pp. 171-174, vol. 22, Czechoslovakia.
Donaldson, J.D., & Knifton, J.F. Tin (II) Formate, J. Chem. Soc. (1964), pp. 4801-4803, U.K.

\* cited by examiner

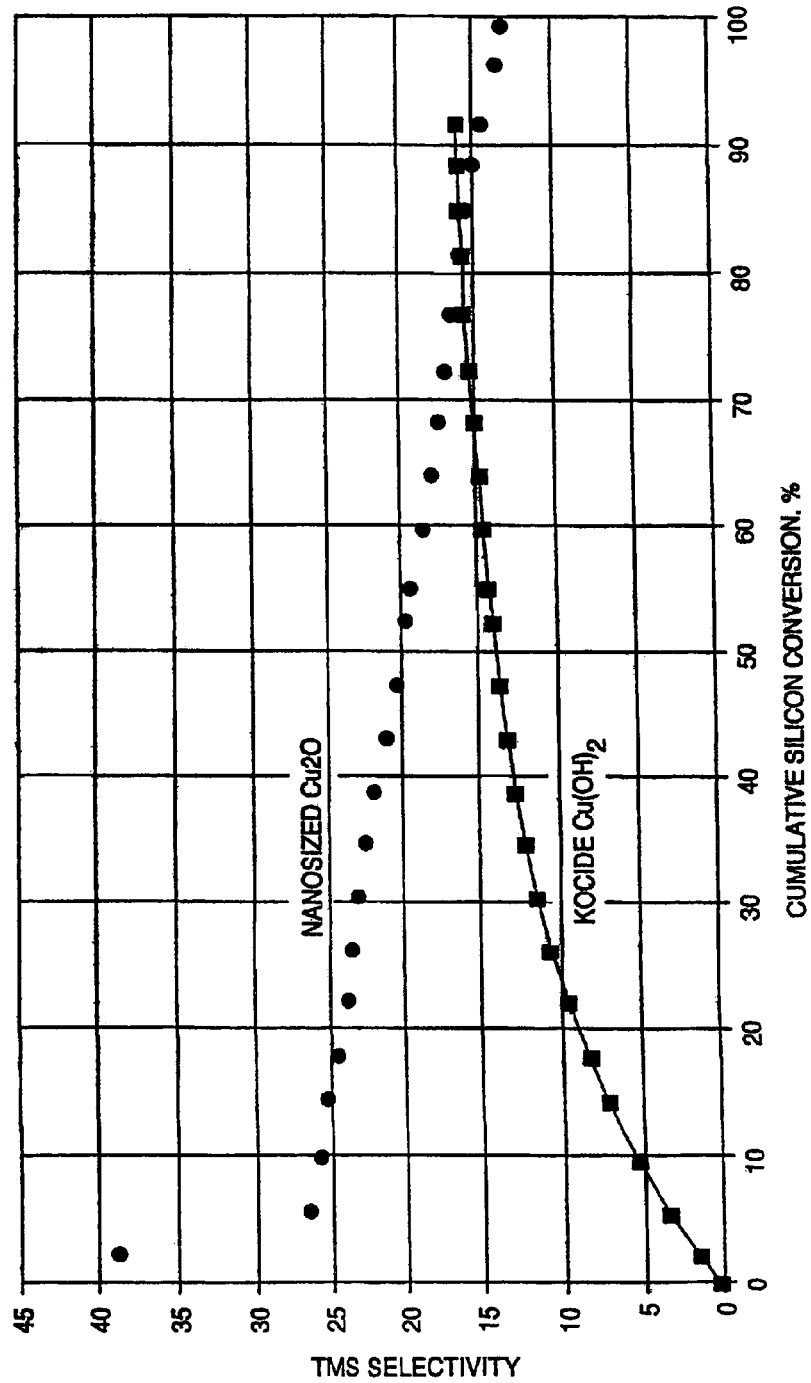

NANOSIZED COPPER CATALYST PRECURSORS FOR THE DIRECT SYNTHESIS OF TRIALKOXYSILANES

This application is a divisional of U.S. patent application Ser. No. 09/974,092 filed Oct. 9, 2001, now U.S. Pat. No. 7,339,068 which claims priority from provisional U.S. Patent Application Ser. No. 60/265,154 filed on Jan. 31, 2001 which is herein incorporated by reference in its entirety.

BACKGROUND OF THE INVENTION

1. Field of the Invention

The present invention relates to the production of trialkoxysilanes by the Direct Synthesis of silicon with alcohols in the presence of a copper catalyst. This Direct Synthesis exhibits short induction times, high selectivity for trialkoxysilanes, high overall silicon conversion, and high, stable reaction rates.

2. Description of Related Art

Trialkoxysilanes, especially trimethoxysilane and triethoxysilane, are used in the production of silane coupling agents. One method of synthesizing trialkoxysilanes is directly from silicon and an alcohol in the presence of copper or a copper compound. This method is known variously in the art as the "Direct Synthesis", the "Direct Reaction," the "Direct Process," or the Rochow Reaction. For trialkoxysilanes, it is most conveniently performed in slurry reactors.

U.S. Pat. No. 3,641,077 to Rochow which issued on Feb. 8, 1972, discloses the Direct Synthesis of trialkoxysilanes in a slurry reactor using catalytically activated silicon particles suspended in a thermally stable, high boiling solvent reacted with an alcohol at an elevated temperature. Trialkoxysilanes were prepared by directly reacting a copper-silicon mass, suspended in a silicone oil, with alcohol at 250 to 300° C. The copper-silicon mass contained about 10 wt. % copper and was prepared by heating copper and silicon at temperatures above 1000° C. in a furnace in the presence of a hydrogen gas stream. Low yields of trialkoxysilanes are generally obtained using this method.

U.S. Pat. No. 3,775,457 to Muraoka et al. which issued on Nov. 27, 1973, teaches the use of polyaromatic hydrocarbon oils as solvents in the Direct Synthesis of trialkoxysilanes from an alcohol and finely divided silicon metal activated with cuprous chloride catalyst. The use of cuprous chloride provides an increased yield over that obtained using the sintered copper-silicon mass taught in U.S. Pat. No. 3,641,077 to Rochow.

The use of cuprous chloride or cupric chloride with alkylated benzene solvents such as dodecylbenzene and tridecylbenzene as disclosed in U.S. Pat. No. 5,362,897 to Harada et al. which issued on Nov. 8, 1994, Japanese Kokai Patent Application 55-28928 (1980), 55-28929 (1980), 55-76891 (1980), 57-108094 (1982) and 62-96433 (1987), also affords increased yields of trialkoxysilanes. It is advantageous to use the alkylated benzene solvents because they are less expensive and less hazardous to people and the environment than the polyaromatic hydrocarbon solvents taught in U.S. Pat. No. 3,775,457.

U.S. Pat. No. 5,362,897 to Harada et al., claims the use of specially prepared "wet process" cuprous chloride, CuCl, in preference to commercial "dry process" cuprous chloride, to afford higher reaction rate and silicon conversion. "Wet process" cuprous chloride is defined therein as that "prepared through the steps of crystallization and separation and drying." "Dry process" cuprous chloride is prepared from metallic copper and chlorine gas. Preferably, the "wet process" cuprous chloride is less than 2 µm in size.

Japanese Kokai Patent Application 11-21288 (1999) discloses the use of wet or dry cuprous chloride to activate silicon metal by heating at 250° C. in a straight chain alkylated benzene solvent for at least 3 hours. The particle size of the cuprous chloride was 0.1 to 50 µm, preferably 0.5 to 10 µm.

The use of copper (II) hydroxide as a catalyst is disclosed in U.S. Pat. No. 4,727,173 to Medicino which issued on Feb. 23, 1988. Limitations associated with cuprous chloride were avoided and high selectivity to trialkoxysilanes was reported. The preferred solvents were diphenyl ether, polyaromatic hydrocarbons like THERMINOL® 59, THERMINOL® 60, THERMINOL® 66, and alkylated benzenes such as dodecylbenzene. However, U.S. Pat. No. 5,728,858 to Lewis et al. which issued on Mar. 17, 1998, discloses that when copper (II) hydroxide is used in combination with alkylated benzene solvents such as dodecylbenzene, the Direct Synthesis becomes unstable after about 25 to 35 wt. % silicon has reacted. When methanol is the alcohol reactant at temperatures over 220° C., trimethoxysilane content in the reaction product declines from approximately 90 to 95 wt. % to 50 to 60 wt. %. After 60 wt. % silicon conversion, the trimethoxysilane content increases to 80 to 95 wt. %. Simultaneous with the loss of selectivity is the enhanced formation of methane, water, and dimethyl ether. Methane and dimethyl ether formation result from the inefficient use of methanol. Water reacts with trialkoxysilanes to produce soluble, gelled and/or resinous organic silicates which cause foaming leading to incomplete recovery of the reaction solvent.

U.S. Pat. No. 5,728,858 to Lewis et al. also teaches the reductive activation of copper (II) hydroxide/silicon slurries with hydrogen gas, carbon monoxide, monosilane or polyaromatic hydrocarbons to obtain active, selective, and stable Direct Synthesis of trialkoxysilanes in alkylated benzene solvents such as the linear alkylate NALKYLENE® 550BL. Particle size of the copper (II) hydroxide is desirably 0.1 to 50 µm, and preferably 0.1 to 30 µm.

The use of hydrogen to activate silicon with copper for the Direct Synthesis is well known in the prior art. Hydrogen activation is accomplished at temperatures above 400° C. in fixed bed reactors, fluidized bed reactors or furnaces with silicon-copper catalyst mixtures containing more than 1.5 wt. % copper. However, the prior art provides little information regarding selectivity, reactivity, and reaction stability of the silicon-copper masses in slurry phase Direct Synthesis of trialkoxysilanes.

In Suzuki et al., *Bulletin of the Chemical Society of Japan*, Vol. 1 (1994) pp. 3445-3447, the hydrogen activation of silicon and cupric chloride mixtures having 2.5 wt. % copper in a fixed bed reactor at 260° C. afforded complete silicon conversion and 89% selectivity to trimethoxysilane in a Direct Synthesis with methanol. The duration of the induction period, reaction rate, and selectivity to the trimethoxysilane were all very dependent on the temperature of the hydrogen activation.

The use of other copper catalysts such as copper alkoxides, with or without copper chlorides, and cupric oxide are also taught in the prior art. However, the prior art does not mention any particular particle size of these copper catalysts.

Alcohol dehydration and dehydrogenation are especially troublesome problems when ethanol and other higher homologs are used in the Direct Synthesis. At temperatures greater than 250° C., alkenes, aldehydes and acetals, and not the desired trialkoxysilanes, are formed in significant amounts. Even when these are not the predominant products, their presence in the reaction mixture may inhibit further catalytic activity. At lower temperatures, (for example 220° C.), alcohol decomposition reactions are less prevalent, but the Direct Synthesis is slower. Japanese Patent Application Kokai 55-2641 (1980) discloses the use of cyclic ethers to improve reactivity and selectivity to triethoxysilane when the Direct Synthesis is conducted in dodecylbenzene at these lower temperatures. However, cyclic ethers such as dibenzo-18-crown-6 are quite expensive; others such as 12-crown-4 are also toxic.

In spite of the improvements and advances taught in the prior art, there continues to exist the need for a stable, highly selective and rapid Direct Synthesis of trialkoxysilanes which produces less waste and avoids the deficiencies of conventionally prepared copper chlorides, alkylated benzene solvents and specially selected silicon samples. In particular, there is a need for such a Direct Synthesis, which eliminates or avoids the alcohol reduction, alcohol dehydrogenation and alcohol dehydration side reactions typical of ethanol and the higher alcohols. There is also a need for a Direct Synthesis of trialkoxysilane which is desirably and acceptably reactive, selective and stable with silicon samples spanning a wide range of manufacturing methods, trace metal concentrations, silicide intermetallic phases, oxygen contents and surface oxidation.

Bearing in mind the problems and deficiencies of the prior art, it is therefore an object of the present invention to provide a Direct Synthesis of trialkoxysilanes from silicon metal and alcohol that has enhanced selectivity to trialkoxysilane over tetraalkoxysilane throughout the entire course of the reaction having high silicon conversion and stable reaction rate, and the resultant trialkoxysilane.

It is another object of the present invention to provide a Direct Synthesis of trialkoxysilanes which produces less waste products and avoids the inefficient-use of the alcohol reactant by eliminating or avoiding the alcohol reduction, alcohol dehydrogenation and alcohol dehydration side reactions when ethanol and higher alcohols are used.

A further object of the invention is to provide a Direct Synthesis of trialkoxysilanes that uses more desirable solvents.

It is yet another object of the present invention to provide a Direct Synthesis of trimethoxysilane and triethoxysilane which is more economically and environmentally viable.

Still other objects and advantages of the invention will in part be obvious and will in part be apparent from the specification.

SUMMARY OF THE INVENTION

The above and other objects and advantages, which will be apparent to one of skill in the art, are achieved in the present invention which is directed to, in a first aspect, a process for using a member selected from the group consisting of nanosized copper, nanosized copper oxides, nanosized copper chlorides, other nanosized copper salts, and mixtures thereof as sources of catalytic copper in the Direct Synthesis of trialkoxysilane of formula $HSi(OR)_3$ wherein R is an alkyl group containing from 1 to 6 carbon atoms inclusive, the process comprising:
(a) forming a reaction mixture comprising a thermally stable solvent, silicon metal, a catalytically effective amount of the nanosized copper catalyst precursor;
(b) agitating and heating this mixture to form copper-activated silicon in situ and injecting into the reaction mixture an alcohol to react with the copper-activated silicon to produce the trialkoxysilane; and
(c) recovering the trialkoxysilane from the reaction product.

Preferably, the process may further comprise step
(d) remediating and reusing the reaction solvent in the Direct Synthesis of trialkoxysilanes.

Preferably, forming the reaction mixture includes mixing with a solvent used in preparation of the nanosized copper catalyst precursor. Preferably, the Direct Synthesis of trimethoxysilane and triethoxysilane occurs with about 300 to about 5000 parts per million copper based on an amount of silicon. The member may be selected from the group consisting of nanosized copper, nanosized copper oxides, nanosized copper chlorides, other nanosized copper salts, and mixtures thereof, has an average particle size in a range from about 0.1 to about 600 nanometers. More preferably, the average particle size is in a range from about 0.1 to about 500 nanometers. Most preferably, the average particle size in a range from about 0.1 to about 100 nanometers.

In a second aspect, the present invention is directed to a process for the Direct Synthesis of trialkoxysilanes comprising the steps of:
(a) providing a slurry of silicon metal, and a copper catalyst precursor having an average particle size of about 0.1 to 600 nanometers in a thermally stable solvent;
(b) forming a copper-silicon intermetallic;
(c) reacting the copper-silicon intermetallic with an alcohol of formula ROH wherein R is an alkyl group having 1 to 6 carbon atoms inclusive, to form a trialkoxysilane of the formula $HSi(OR)_3$ wherein R is as previously defined;
(d) recovering the trialkoxysilane; and
(e) remediating the thermally stable solvent for subsequent Direct Synthesis of trialkoxysilanes.

Preferably, in step (a) the slurry is formed with nanosized silicon metal which may be produced by acid leaching, and wherein the copper catalyst precursor comprises nanosized copper chloride. The thermally stable solvent may be a member selected from the group consisting of linear and branched paraffins, cycloparaffins, alkylated benzenes, aromatic ethers, and polyaromatic hydrocarbons. Preferably, in step (a), an initial copper concentration is about 300 to about 5000 ppm based on an amount of the silicon metal, and the copper catalyst precursor may have an average particle size of about 0.1 to 100 nanometers. The copper catalyst precursor is preferably selected from the group consisting of nanosized copper, nanosized copper oxides, nanosized copper chlorides, other nanosized copper salts, and mixtures thereof.

Preferably, in step (b) the copper-silicon intermetallic is formed by heating the copper catalyst precursor in the slurry for about 0.01 to about 24 hours at a temperature of about 20 to about 400° C. In step (b) the copper-silicon intermetallic can be formed in situ or in a separate reaction vessel prior to reaction with the alcohol.

Preferably, in step (d) the alcohol is introduced as a gaseous stream to react with the copper-silicon intermetallic. It is possible to provide more than one alcohol is present to react with the copper-silicon intermetallic.

In a third aspect, the present invention is directed to a composition useful for the Direct Synthesis of trialkoxysilanes comprising: silicon metal having a particle size of less than about 500 µm; one or more copper catalyst precursors having an average particle size from about 0.1 nm to about 600 nm, a surface area as low as 0.1 m²/g, in an amount from about 0.01 to about 5 parts by weight per 100 parts of the silicon metal such that about 0.008 to about 4.5 parts elemental copper is present based on 100 parts by weight of the silicon metal; and a thermally stable reaction solvent present in an amount that provides a gravimetric ratio of solids to solvent of about 1:2 to about 1:4. Preferably, the copper catalyst precursors are selected from the group consisting of copper metal, copper (I) oxide, copper (II) oxide, copper (I) chloride, copper (II) chloride, copper (I) carboxylates, copper (II) carboxylates, other copper salts, and mixtures thereof.

In a third aspect, the present invention is directed to a method of controlling Direct Synthesis of trialkoxysilanes comprising the steps of:
 providing a silicon metal;
 providing a thermally stable solvent;
 providing one or more copper catalyst precursors having an average particle size of less than 600 nm;
 heating the silicon metal and the one or more copper catalyst precursors in the thermally stable solvent;
 forming copper-silicon intermetallics for reaction with an alcohol; and
 maintaining an effective copper concentration during a steady state of the Direct Synthesis wherein selectivity for trialkoxysilanes is greater than about 10.

The present invention is also directed to the resultant trialkoxysilanes made from the methods discussed above.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

FIG. 4 shows a comparison of the selectivity in the product versus silicon conversion for the Direct Synthesis of HSi(OCH$_3$)$_3$ with nanosized copper (I) oxide and KOCIDE® copper (II) hydroxide having 57 to 59 wt. % copper.

DESCRIPTION OF THE PREFERRED EMBODIMENT(S)

Figure 1:
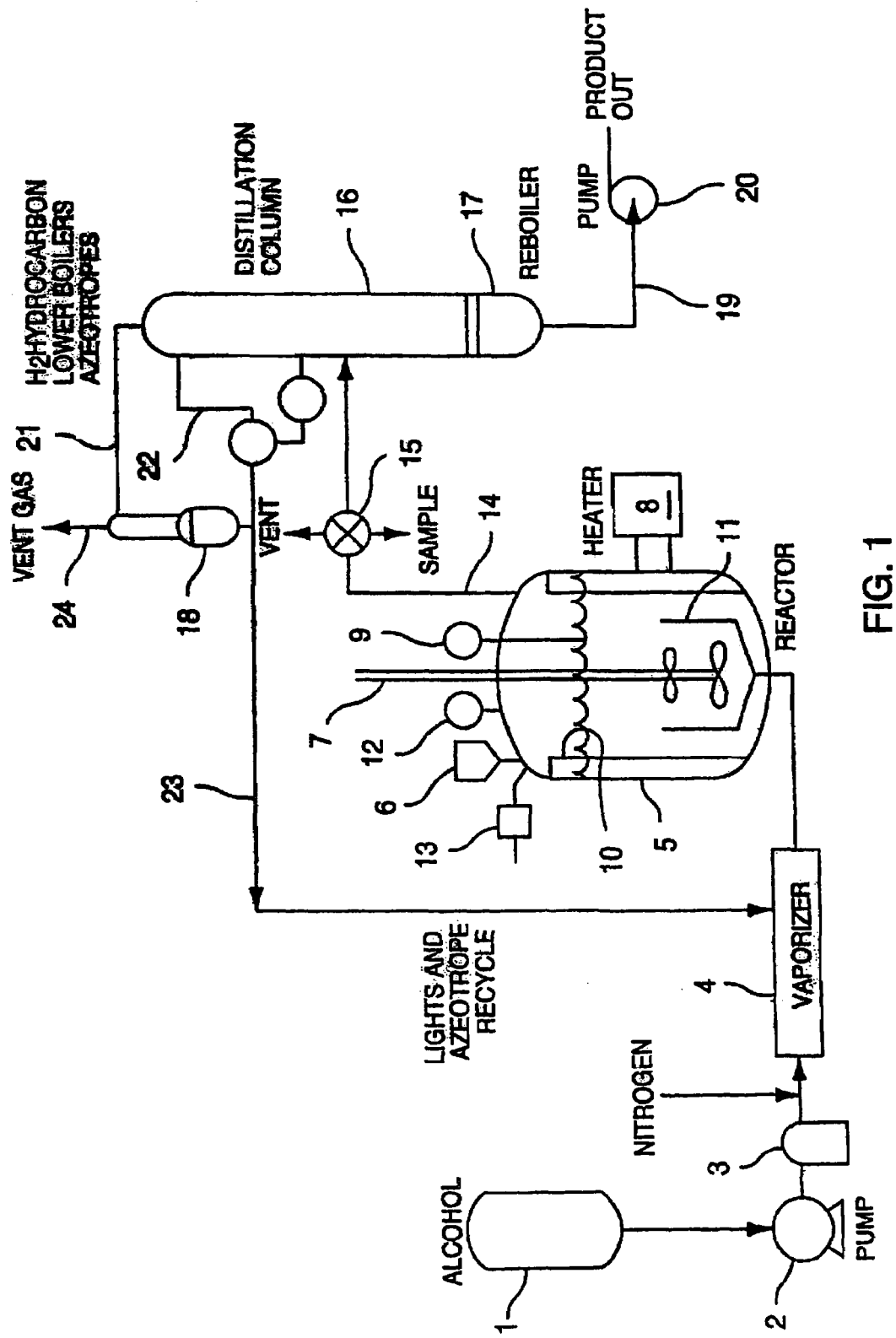
FIG. 1 is a schematic representation of a slurry reaction apparatus for the Direct Synthesis of trialkoxysilanes.
Figure 2A:
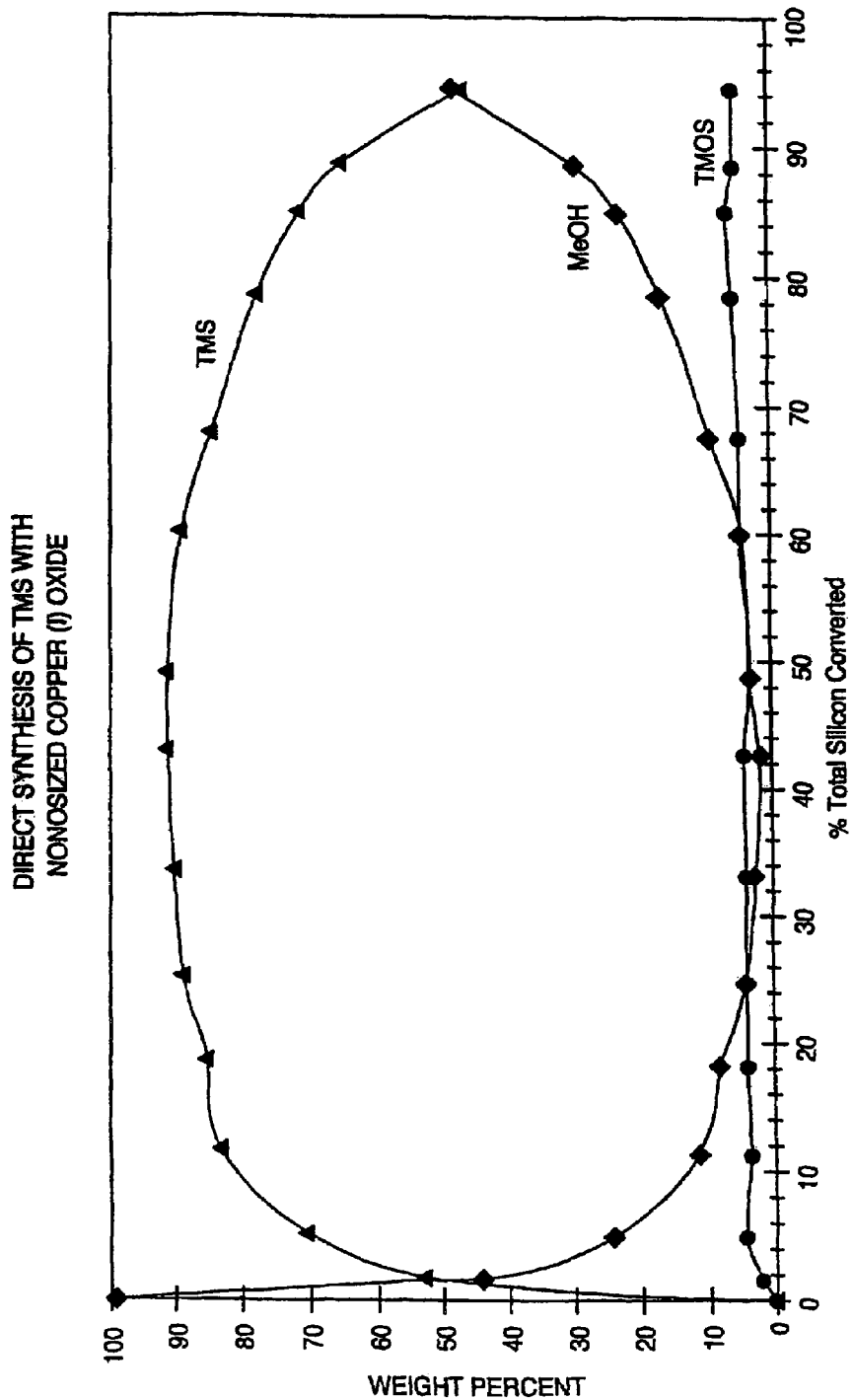
FIG. 2A is a plot of the composition of the reaction mixture during the Direct Synthesis of trimethoxysilane, HSi(OCH$_3$)$_3$ with nanosized copper (I) oxide, Cu$_2$O, in accordance with the present invention.
Figure 2B:
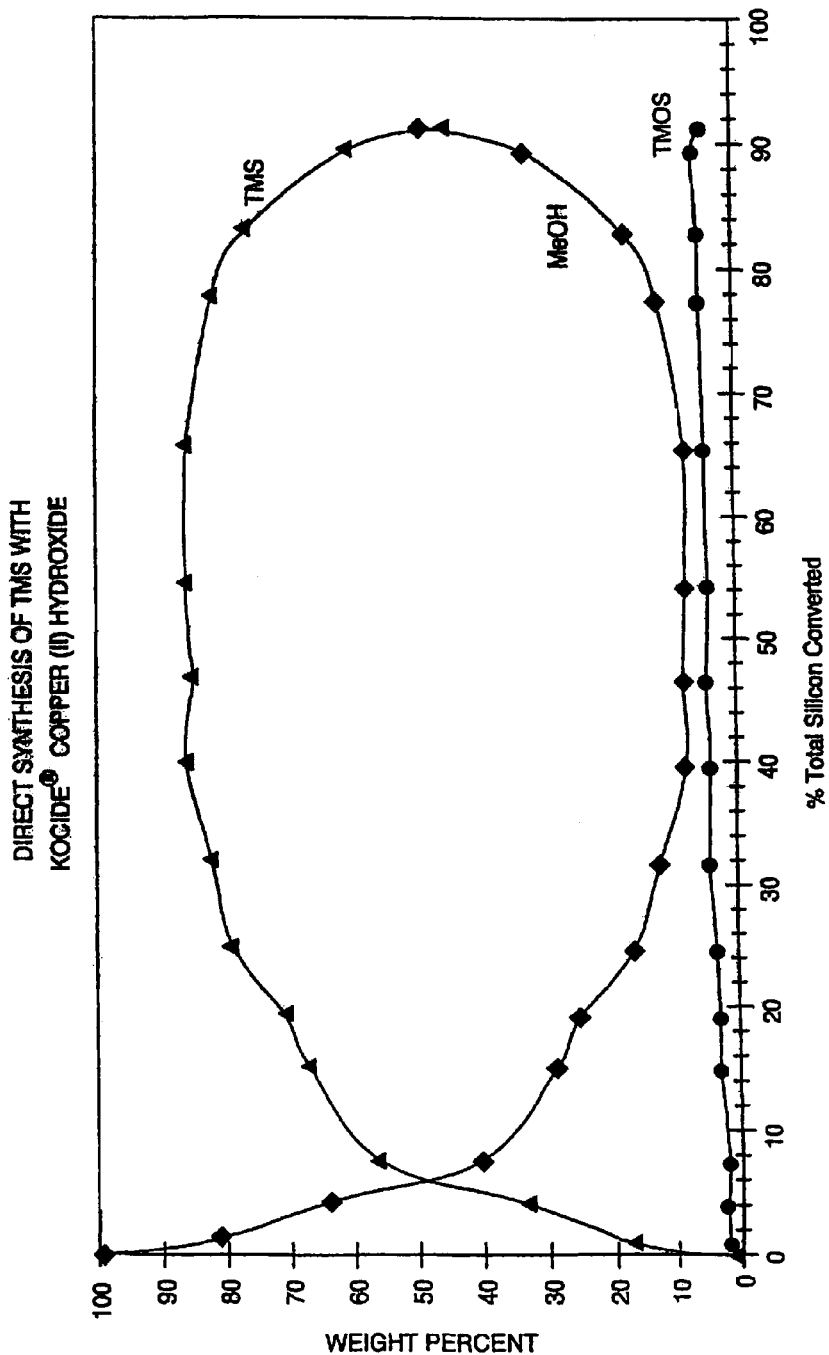
FIG. 2B is a plot of the composition of the reaction mixture during the Direct Synthesis of trimethoxysilane with KOCIDE® copper (II) hydroxide having 57 to 59 wt. % copper, in accordance with U.S. Pat. No. 4,727,173 to Mendicino as a comparison.

In describing the preferred embodiment of the present invention, reference will be made herein to FIGS. 1-4 of the drawings in which like numerals refer to like features of the invention. Features of the invention are not necessarily shown to scale in the drawings.

The invention provides a method of using nanosized copper, nanosized copper oxides, nanosized copper chlorides, other nanosized copper salts, and mixtures thereof, as sources of catalytic copper in the Direct Synthesis of trialkoxysilanes having the formula HSi(OR)$_3$ wherein R is an alkyl group containing from 1 to 6 carbon atoms inclusive. The nanosized copper, nanosized copper oxides, nanosized copper chlorides, other nanosized copper salts, and their mixtures which are used in the present invention, have average particle sizes that are in the range from about 0.1 to about 600 nanometers, preferably from about 0.1 to about 500 nanometers, and most preferably from about 0.1 to about 100 nanometers. Nanosized sources of catalytic copper afford high dispersion of catalytic sites on silicon and contribute to high reaction rates, high selectivity and high silicon conversion.

The process comprises (a) forming a reaction mixture comprising a thermally stable solvent, silicon metal, a catalytically effective amount of the nanosized copper catalyst precursor, optionally mixed with the solvent used in its preparation, (b) agitating and heating this mixture to form copper-activated silicon in situ and injecting into it an alcohol of formula ROH, to react with the copper-activated silicon to produce a trialkoxysilane, (c) recovering the trialkoxysilane from the reaction product, and, optionally, (d) remediating and reusing the reaction solvent in the Direct Synthesis of trialkoxysilanes.

The present process affords shorter induction times, higher selectivity to the trialkoxysilanes even after high silicon conversion higher reaction rates, higher overall silicon conversion, and better reaction stability compared to state-of-the-art processes.

The present process also achieves desirably acceptable performance with chemical grade silicon samples from a wide variety of sources and suppliers. Additionally, significant hydrocarbon, water, dialkyl ether and polysilicate formation is prevented, and considerably less process waste is produced. The process produces trialkoxysilanes at high rates and in quantity such that, in batchwise operation, the overall gravimetric ratios of trialkoxysilane to tetraalkoxysilane are greater than about 9 to 1, even after multiple batches of silicon have been reacted in a single solvent charge. Thus, this Direct Process results in high overall conversion of silicon and alcohol to desirable products. Furthermore, nanosized copper and nanosized copper oxides are halogen-free and do not generate corrosive acids or salts in the reactor and transport lines. Thus, costly materials of construction are not required for the reactor and its ancillary parts, when these halogen-free, superfine copper sources are used.

The nanosized copper catalyst precursors of the invention permit the use of substantially reduced levels of copper compared to conventional practice. Conventional levels of copper are greater than 1 wt. % or 10,000 parts per million (ppm) based on the amount of silicon. With the nanosized copper catalyst precursors of this invention, stable, selective and controllably reactive Direct Synthesis of trimethoxysilane and triethoxysilane are attainable with about 300 to about 5000 ppm total copper or about 0.03 to about 0.5 wt. % based on silicon.

The following equations are representations of the principal chemical reactions occurring during the Direct Synthesis of trialkoxysilanes.

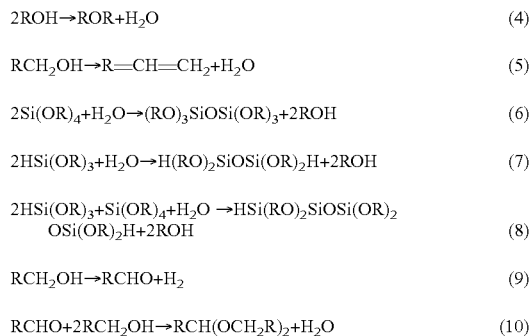

$$2ROH \rightarrow ROR + H_2O \quad (4)$$

$$RCH_2OH \rightarrow R=CH=CH_2 + H_2O \quad (5)$$

$$2Si(OR)_4 + H_2O \rightarrow (RO)_3SiOSi(OR)_3 + 2ROH \quad (6)$$

$$2HSi(OR)_3 + H_2O \rightarrow H(RO)_2SiOSi(OR)_2H + 2ROH \quad (7)$$

$$2HSi(OR)_3 + Si(OR)_4 + H_2O \rightarrow HSi(RO)_2SiOSi(OR)_2OSi(OR)_2H + 2ROH \quad (8)$$

$$RCH_2OH \rightarrow RCHO + H_2 \quad (9)$$

$$RCHO + 2RCH_2OH \rightarrow RCH(OCH_2R)_2 + H_2O \quad (10)$$

The desirable products of the instant Direct Synthesis are trialkoxysilanes of the general formula, $HSi(OR)_3$, wherein R is an alkyl group of 1 to 6 carbon atoms. R is preferably methyl and ethyl. Byproducts of the synthesis are $Si(OR)_4$, $RSiH(OR)_2$, $RSi(OR)_3$, linear, branched and cyclic silicates such as $(RO)_3SiOSi(OR)_3$, $H(RO)_2SiOSi(OR)_2H$, $HSi(RO)_2SiOSi(OR)_3$, $(RO)_3SiOSi(OR)_2R$, $(RO)_3SiOSi(RO)_2OSi(RO)_3$, —$(RO)_3SiOSi(OR)HOSi(OR)_3$, $(RO)_3SiOSi(OR)ROSi(OR)_3$, $(RO)Si[OSi(OR)_3]_3$, $(RO)_3SiOSi(OR)(OSi(RO)_3)OSi(OR)_3$, $[OSi(OR)_2]_n$ wherein n is 4, 5, etc., hydrogen gas, hydrocarbons (RH) such as methane and ethane, alkenes ($R'=CH=CH_2$) such as ethylene, ethers (ROR) such as dimethyl ether and diethyl ether, aldehydes (RCHO) such as acetaldehyde and acetals ($RCH(OCH_2R)_2$) such as 1,1-diethoxyethane. In the general formula, $R'=CH=CH_2$, for the alkene byproducts, R' is hydrogen or an alkyl group of 1 to 4 carbon atoms. Hydrogen gas, hydrocarbons, volatile aldehydes and the ethers are typically not condensed in the cold trap with the liquid products and exit the apparatus as a gaseous stream. Some of the silicates are volatilized out of the reactor or are soluble in the liquid reaction product. Others remain solublized in the solvent or precipitate as insoluble gels. The acetals ($RCH(OCH_2R)_2$) and less volatile aldehydes are condensed in the liquid reaction mixture.

When the Direct Synthesis is conducted in accordance with the present invention, trialkoxysilanes comprise at least 80 wt. %, preferably at least 85 wt. %, of the liquid reaction products. Typical levels of the alkyl silicates, $Si(OR)_4$, are less than 9 wt. %, and preferably less than 6 wt. %. $(RO)_2SiH_2$, $RSiH(OR)_2$ and $RSi(OR)_3$ compounds are individually less than 2 wt. %, and preferably less than 1 wt. %. Condensed silicates are maximally 1 wt. %, and preferably, less than 0.5 wt. %.

In addition to the percentage ranges taught hereinabove, selectivity to the desired trialkoxysilanes may also be expressed as the gravimetric ratio $HSi(OR)_3/Si(OR)_4$. By the method of the invention, this ratio is at least 9 when computed over the total course of a reaction. This overall value is also referred to herein as the product selectivity to distinguish it from the selectivity of individual samples taken during the course of a reaction. It is, preferably, at least 15 and it might attain values greater than 30, especially at the outset and during the steady-state portion of the reaction.

Gas chromatographic (GC) analysis has been found to be a reliable and accurate technique to quantify the composition of the liquid reaction product. Other methods such as nuclear magnetic resonance (NMR) and mass spectrometry (MS) may also be used. These are particularly useful for identifying and quantifying the higher molecular weight silicates contained in the reaction product and reaction solvent. Data on the composition and weight of the reaction product and the fraction of silicon in each of the components are used to calculate the silicon conversion.

Reaction rate is typically expressed as silicon conversion per unit time, but it might also be expressed as alcohol conversion per unit time. It is desirable to have reaction rates, which provide a good balance between product formation and heat removal (temperature control) in the reactor. Rates greater than about 4 wt. % silicon conversion per hour, preferably between about 5 to about 20 wt. % silicon conversion per hour are desired and obtainable with the instant process. It is also desirable that the induction time, that is the interval between the onset of reaction and the attainment of both steady-state rate and product composition, be very short, preferably less than about 4 hours and most preferably less than about 1 hour. The gaseous product stream contains hydrogen gas, hydrocarbons, ethers and inerting agents such as nitrogen or argon. Analytical methods based on gas chromatography, Fourier Transform Infra-red spectroscopy (FTIR) or mass spectrometry may be used to identify and quantify these components in the gaseous effluent. Assuming that the reaction of Equation 1 produces most of the hydrogen gas in the effluent, the hydrogen generated in the Direct Synthesis may be used as an approximate measure of reaction rate and silicon conversion. Hydrocarbon and ether formation depicted in Equations 3 and 5, and aldehyde and acetal formation in Equations 9 and 10 may be used as measures of the inefficiency of alcohol conversion. It is desirable that less than about 2 wt. % of the alcohol fed to the reaction be converted to hydrocarbons, ethers, aldehydes and acetals and most desirable that none be so converted.

Gravimetry and atomic absorption spectroscopy are suitable methods for quantifying the silicon content of the reaction solvent. Analytical procedures are published, for example, in Smith, A. L., Ed., *The Analytical Chemistry of Silicones*, John Wiley & Sons Inc., NY, (1991), chapter 8. Soluble silicates retained in the reaction solvent are a measure of the extent to which side reactions such as those in Equations 6 to 8 have occurred. All of these reactions depend on the presence of water, which is formed, for example, by the reaction of Equations 3 to 5 and 10. Gels and soluble silicates contained in the reaction solvent may be removed according to the methods disclosed in U.S. Pat. No. 5,166,384 to Bailey, et al. which issued on Nov. 24, 1992, or U.S. Pat. No. 6,090,965 to Lewis, et al. which issued on Jul. 18, 2000.

The nanosized copper and/or nanosized copper compounds useful as starting materials for the preparation of the trialkoxysilanes are not themselves the actual catalysts for the instant Direct Synthesis invention. When the slurry comprising the nanosized copper and/or nanosized copper compound, silicon and a reaction solvent is heated, the copper and silicon interact to produce the actual catalytic phase that reacts with the alcohol. It is generally accepted that the actual catalysts in Direct Reactions of silicon are the copper-silicon alloys or intermetallics and solid solutions formed by the diffusion of copper into silicon, or by the reaction of copper compounds with silicon. Thus, the nanosized, copper-containing raw materials are all catalyst precursors and will be referred to as such.

Nanosized Copper Catalyst Precursors

Nanosized copper catalyst precursors of the present invention comprise copper, copper (I) oxide, copper (II) oxide, copper (I) chloride, copper (II) chloride, copper (I) carboxylates, copper (II) carboxylates, other copper salts, and mixtures thereof, having an average particle size from about 0.1 to about 600 nanometers, preferably from about 0.1 to 500 nanometers, and most preferably from about 0.1 to 100 nanometers. Various physical and chemical methods have been disclosed in the prior art for the synthesis of these superfine solids. Nanosized material produced by these physical and chemical methods is usable in the process of the invention provided that it does not impair the selectivity, rate and/or stability of the Direct Synthesis of the trialkoxysilanes.

Physical methods include, but are not limited to, preparation by milling, sputtering, ion bombardment, laser ablation and evaporation. When a physical method is used to prepare the nanosized copper catalyst precursors, it is desirable, but not essential, that the particles be collected in the reaction solvent, or on the silicon to be reacted as they are generated. For example, laser ablation of powdered copper compounds, like CuCl and CuO, may be performed in the reaction solvents. Additionally, nanometer sized clusters of copper and copper compounds generated by evaporation, sputtering or ion bombardment may be collected on silicon. Copper-silicon intermetallics and solid solutions may thereby be formed. The clusters may also be quenched in the reaction solvents to be used. If additives, such as surfactants and polymers, are used for stabilization against sintering and agglomeration, they must not impair the selectivity, rate and stability of the Direct Synthesis of trialkoxysilanes. Some silicones, organofluoro surfactants and fluorosilicone surfactants known to be useful foam control agents in the art might also be helpful in dispersing the nanoparticles.

State-of-the-art chemical methods have used solid state reactions, reduction in reversed micelles and microemulsions, reduction in polyols, or electrochemical oxidation to produce nanosized copper and nanosized copper compounds. A most preferred method of making nanosized copper catalyst precursors for use in the Direct Synthesis of trialkoxysilanes comprises the thermal decomposition, dehydration and/or reduction of copper hydroxide, copper alkoxides, copper carbonates, copper carboxylates, other copper precursors and their mixtures in hydrocarbons at temperatures greater than 150° C.

Nanosized copper catalyst precursors for use in the invention are preferably anhydrous, but material containing adventitious water or water of hydration is also usable. If a hydrated, nanosized copper catalyst precursor is used, provision must be made in the design of the reaction apparatus to avoid contact of the water formed during its dehydration and thermal decomposition with the trialkoxysilane reaction product. Additionally, alcohol introduction into the reaction slurry must be delayed until the dehydration and thermal decomposition are complete. This is usually at temperatures greater than about 150 to about 180° C.

In addition to particle size and water content, various other criteria may be used to characterize the nanosized copper catalyst precursors of this invention. BET surface area of the precursors may be as low as 0.1 m$^2$/g. Areas greater than 10 m$^2$/g are preferred and greater than 15 m$^2$/g are particularly preferred.

Trace impurities and extraneous matter might be present in the nanosized copper catalyst precursors depending on the method and conditions of its preparation. Thus, trace amounts of aluminum; barium, calcium, lead, phosphorus, tin and zinc might be present in the nanoparticulate copper and copper oxides. Tolerable and limiting quantities of the pertinent metals are defined below. Polymers, surfactants and boron contamination might be present in nanoparticulate copper generated by borohydride reduction in the presence of stabilizing polymers, or in reverse micelles and microemulsions.

The presence of excessive tin in the reaction has adverse effects on the reaction rate and/or the selectivity for trialkoxysilane and as such excessive tin levels should be avoided. It is desirable that the tin content of the copper catalyst precursor be less than about 1000 ppm, preferably that it be less than about 300 ppm, and most preferably that it be less than about 100 ppm based on the amount of silicon. Of greater importance is the tin content of the reaction slurry. Based on the weight of silicon at the outset of a reaction, it is desirable that the tin content be less than about 100 ppm, and preferable that it be less than about 10 ppm.

Zinc content of the copper catalyst precursor is desirably less than about 2500 ppm, and preferably less than about 1500 ppm based on the amount of silicon. Based on the initial weight of silicon charged to the reactor, zinc content of the reaction slurry must be less than about 100 ppm, and preferably less than about 50 ppm.

The other critical trace element, which may be contained in the catalyst precursor, is lead. Its concentration in the slurry must be less than about 50 ppm.

The nanosized copper catalyst precursors used in the Direct Process of this invention are present in an amount effective to catalyze the reaction. Generally, an effective amount ranges from about 0.01 to about 5 parts by weight of catalyst precursor per 100 parts by weight of the silicon metal. The smaller particle size and higher surface area of the nanosized copper catalyst precursors of the invention afford higher dispersion of the actual catalytic phases on the silicon surface. Accordingly, usage of nanosized copper catalyst precursors in amounts in the lower part of this range is unusually effective in initiating and sustaining selective synthesis of trialkoxysilanes. Thus, 0.05 to about 2 parts by weight of the nanosized copper catalyst precursor per 100 parts by weight silicon is preferred, and about 0.08 to about 1 part by weight per 100 parts by weight silicon is especially preferred. Expressed in terms of parts by wt. % copper per 100 parts by weight silicon, the effective range is about 0.008 to about 4.5 parts copper, the preferred range is about 0.03 to about 1.8 parts copper, and the especially preferred range is about 0.05 to about 0.9 parts copper.

Silicon

The silicon metal reactant used in the process of this invention may be any commercially available grade of silicon in particulate form. It may be produced by any of the methods known in the art such as casting, water granulation, atomization and acid leaching.

Special types of chemical grade silicon containing controlled concentrations of alloying elements are also suitable, provided that copper is not one of the alloying elements and that the alloying elements are not deleterious to the rate, selectivity and stability of the Direct Synthesis of trialkoxysilane. A typical composition of commercial silicon metal useful in this invention, expressed in percent by weight, is about 98.5 wt. % silicon, less than about 1 wt. % iron, about 0.05 to about 0.07 wt. % aluminum, about 0.001 to 0.1 wt. % calcium; less than about 0.001 wt. % lead, and less than about 0.1 wt. % water. Generally, smaller particle sizes are preferred for ease of dispersion in the slurry, faster reaction and minimization of erosion in the reactor. Preferably, there are no particles larger than 500 μm so that reactor erosion is minimized. Sieving of ground silicon to regulate particle size is optional. A particle size distribution, wherein at least 90 wt. % is between about 1 to about 300 μm is preferred. Especially preferred is a distribution in which at least 90 wt. % of the silicon particles is between about 1 to about 100 μm. More preferred is a particle size distribution wherein at least 90 wt. % of the silicon particles is less than 1,000 nanometers. Most preferred is a particle size distribution wherein at least 50 wt. % of the silicon particles is between 1 and 600 nanometers.

One of the advantages of the nanosized copper catalyst precursors of the invention is the marked improvement they effect in the reactivity and conversion of silicon produced by acid leaching. Preparation of silicon of this type is known in the art. An example of this type of silicon is SILGRAIN® from Elkem ASA of Oslo, Norway. For reasons that still remain obscure, this type of silicon does not afford good yields of trialkoxysilanes when activated with CuCl using the method of U.S. Pat. No. 3,775,457 to Muraoka et al. or with Cu(OH)$_2$ by the method of U.S. Pat. No. 4,727,173 to Mendicino or with silicon-copper contact mixtures prepared at 1050° C. in the presence of hydrogen taught in Newton, W. E. et al., *Inorganic Chemistry*, 9 (1970) pp. 1071-1075. However, with nanosized copper and nanosized copper chloride in the Direct Synthesis of trimethoxysilane, selectivity greater than 9 may be sustained beyond 85% silicon conversion, whereas with the method of U.S. Pat. No. 4,727,173 to Mendicino, selectivity and activity decline to substandard values by 67% silicon conversion. The improved performance of nanosized copper catalyst precursors with SILGRAIN® is presented in more detail in the illustrative examples.

Alcohol Reactant

The alcohols which are useful in the process of this invention are those of the formula ROH wherein R is an alkyl group containing from 1 to 6 carbon atoms, inclusive. Preferably R is an alkyl group containing from 1 to 3 carbon atoms inclusive. The most preferred alcohols are methanol and ethanol. While it is customary to use a single alcohol in the Direct Process, mixtures of two or more alcohols may also be used to prepare trialkoxysilanes with different alkoxy groups, or to facilitate the reaction of a less reactive alcohol. For example, about 5 wt. % methanol may be added to ethanol to improve the rate and stability of the Direct Synthesis of triethoxysilane. Alternatively, the reaction may be initiated with one alcohol and continued with another, or with a mixture. Thus, copper-activated silicon prepared with nanosized copper catalyst precursors according to the present invention may be reacted initially with methanol and later with ethanol. It is preferable that the alcohol be anhydrous. However, water contents of up to 0.1 wt. % are tolerated without significant loss of selectivity, reactivity and stability.

Generally, the reaction is run batchwise in a slurry and the alcohol is fed into the slurry as a gas or liquid. Gaseous introduction is preferred. An induction period lasting from a few minutes up to about five hours may be observed. The initial alcohol feed rate is optionally controlled at a low level and increased following the induction period. Similarly, the alcohol feed rate is optionally reduced after about 70% silicon conversion to minimize the formation of tetraalkoxysilanes. Once the reaction is running, the alcohol feed rate may be adjusted to give the desired level of alcohol conversion. One skilled in the art may readily adjust the feed rate in a given reaction by monitoring the product composition. If the feed rate is too high the product stream will contain a larger proportion of unreacted alcohol.

Reaction Solvents

Solvents for the slurry-phase Direct Synthesis of trialkoxysilanes maintain the copper-activated silicon in a well-dispersed state and facilitate mass transfer of the alcohol to catalytic sites. The solvents useful in the process of this invention are thermally stable compounds or mixtures that do not degrade under the activation and reaction conditions. Structurally, they are linear and branched paraffins, cycloparaffins, alkylated benzenes, aromatic ethers, and polyaromatic hydrocarbons. In the latter, the aromatic rings may be fused together as in naphthalene, phenanthrene, anthracene and fluorene derivatives. They may be joined by single carbon-carbon bonds as in biphenyl and terphenyl derivatives, or they may be joined by bridging alkyl groups as in the diphenylethanes and tetraphenylbutanes. One class of preferred solvents is the high temperature stable organic solvents typically used as heat exchange media. Examples include THERMINOL® 59, THERMINOL® 60, THERMINOL® 66, DOWTHERM® HT, MARLOTHERM® S, MARLOTHERM® L, diphenyl ether, diphenyl and terphenyl and their alkylated derivatives with normal boiling points higher than about 250° C.

Structurally, the polyaromatic hydrocarbons useful in the present invention possess two or more aromatic rings with one or more alkyl or cycloalkyl group substituents. The aromatic rings may be fused together as in naphthalene, phenanthrene, anthracene, and fluorene derivatives. They may be joined by single carbon-carbon bonds as in biphenyl and terphenyl derivatives, or they may be joined by bridging alkyl groups as in the diphenylethanes and tetraphenylbutanes.

The preferred polyaromatic hydrocarbons are high temperature stable organic materials typically used as heat exchange media. Examples include THERMINOL® 59, THERMINOL® 60, and THERMINOL® 66 from Solutia, Inc., St. Louis, Mo.; DOWTHERM® HT from Dow Chemical Co., Midland, Mich.; MARLOTHERM® S and MARLOTHERM® L from Condea Chemie GmbH, Marl, Germany; and diphenyl ether having normal boiling points above 250° C. THERMINOL® 59 is a mixture of alkyl-substituted aromatic compounds recommended for use between −45 to 315° C. THERMINOL® 60 is a mixture of polyaromatic compounds with an average molecular weight of about 250. Its optimum temperature range is from −45 to 315° C. as well. THERMINOL® 66 and DOWTHERM® HT are mixtures of hydrogenated terphenyls with an average molecular weight of about 240 and a maximum temperature limit of about 370° C. MARLOTHERM® S is a mixture of isomeric dibenzylbenzenes, and MARLOTHERM® L is a mixture of isomeric benzyl toluenes. Both may be used at temperatures up to about 350° C. Especially preferred are THERMINOL® 59, THERMINOL® 66, DOWTHERM® HT, MARLOTHERM® S, and MARLOTHERM® L.

Suitable alkylated benzenes for the practice of the instant Direct Process are dodecylbenzene, tridecylbenzene, tetradecylbenzene and their mixtures such as are sold by Sasol Chemical Industries, Ltd. of South Africa under the trade names NALKYLENE®, and ISORCHEM®. NALKYLENE® 550BL, NALKYLENE® 500, NALKYLENE® 550L, and NALKYLENE® 600L are particularly preferred hydrocarbon solvents of the present invention for use with the nanosized CuCl precursors. SIRENE® X11L, SIRENE® X12L, and ISORCHEM® 113, available form Ciba-Geigy of Sweden, are also preferred hydrocarbon solvents of the present invention. With nanosized copper and nanosized copper oxides, the alkylated benzene solvents afford better selectivity and stability when used at temperatures between 180 to 220° C.

Cycloparaffins are components of white mineral oils, petroleum distillates and some fuels. White mineral oils and petroleum distillates also contain normal and branched paraffins (see Debska-Chwaja, A. et al., *Soap, Cosmetics and Chemical Specialties*, (November 1994), pp. 48-52; ibid., (March 1995) pp. 64-70). Suitable examples of commercial products containing cycloparaffins and paraffins useful as reaction solvents for this invention are the white mineral oils, CARNATION® 70, KAYDOL®, LP-100 and LP-350, and the petroleum distillates, PD-23, PD-25 and PD-28, all of which are sold by Crompton Corporation under the WITCO® trade name. Other examples of cycloparaffins useful as reaction solvents are butylcyclohexane, decahydro-naphthalene, perhydroanthracene, perhydrophenanthrene, perhydrofluorene and their alkylated derivatives, bicyclohexyl, perhydroterphenyl, perhydrobinaphthyl and their alkylated derivatives.

Mixtures of alkylated benzenes, cycloparaffins, normal and branched paraffins, and polyaromatic hydrocarbons are also useful as reaction solvents for the invention.

Used solvents may be treated with boric acid, borates, formic acid, or by thermal hydrolysis as is known in the art and reused in subsequent trialkoxysilane Direct Synthesis reactions.

Silicon metal, copper (I) oxide and solvent may be added together in the reactor in any order. The solvent is present in an amount sufficient to disperse the solid and gaseous reactants homogeneously. Generally, reactions are initiated with solids to solvent in a gravimetric ratio between 1:2 and 1:4, preferably 1:1 to 1:2. However, as the silicon is consumed during batchwise Direct Synthesis, the solvent to solids ratio will increase. The ratio can be maintained within narrow limits of the preferred range for continuous reactions.

Activation

Activation is the process of incorporating catalyst, and if desired, other auxiliary agents, into the silicon to make it reactive with the alcohol. Activation may be performed in the same reactor used for the Direct Reaction of the alcohol, or in a separate reactor. In the latter case, the activated silicon is typically and desirably transported to the synthesis reactor in an anhydrous, non-oxidizing atmosphere. Transportation of the activated silicon as a slurry in the reaction solvent is especially preferred.

Activation of nanosized copper catalyst precursors and silicon in a slurry reactor is performed at temperatures of about 20 to 400° C., preferably between about 150 to 300° C., with mixtures containing about 0.01 to 50 wt. % copper relative to silicon. In one embodiment, the agitated slurry is heated to about 200 to about 300° C. in an inert gas (for example, nitrogen or argon) atmosphere for about 0.01 to about 24 hours prior to the injection of the alcohol reactant. Time and temperature must be sufficient to bring about effective copper-silicon activation and avoid significant loss of trialkoxysilane selectivity, and/or formation of hydrocarbons and water during the Direct Synthesis. It is not necessary that all of the silicon be present during the activation step. For example, a portion of the silicon to be used and all of the nanosized copper catalyst precursor may be activated in the reaction solvent and the remaining silicon added thereafter.

Alternatively, alcohol, optionally admixed with inert gas, is introduced into the agitated slurry of nanosized copper catalyst precursor, silicon and reaction solvent during heating. Reaction ensues beyond some minimum temperature, typically greater than about 180° C. at atmospheric pressure. Preferably, alcohol vapor is introduced into an agitated slurry after the temperature is greater than or equal to 180° C.

Activation may also be performed with the silicon and nanosized copper catalyst precursors in their dried state in rotary, vibrating, fluidized bed or fixed bed reactors. Thereafter, the activated silicon is transported to the slurry reactor for reaction with the alcohol. Activation of mixtures containing silicon and nanosized copper catalyst precursors may produce water, aldehydes, carbon monoxide, HCl, silicon tetrachloride and other compounds, depending on the specific precursor charged. These compounds are preferably volatilized and absent prior to the start of the Direct Synthesis of the trialkoxysilanes. If they are present in the synthesis reactor or in the product retention vessel, they typically contribute to gel formation, poor reaction selectivity and reduced trialkoxysilane recovery. When nanosized CuCl, or another halogen-containing nanosized copper catalyst precursor, is used, provision must be made to protect the reactor and ancillary equipment from corrosion.

Reactors may be operated in a batchwise or continuous mode. In batchwise operation, a single addition of silicon and copper catalyst is made to the reactor at the outset and alcohol is added continuously, or intermittently, until the silicon is fully reacted, or reacted to a desired degree of conversion. In continuous operation, silicon and copper catalyst are added to the reactor initially and thereafter to maintain the solids content of the slurry within desired limits.

Operation

In the most preferred embodiment in accordance with the present invention, the Direct Synthesis of trialkoxysilanes is conducted in a continuously agitated slurry reactor containing solvent, silicon, nanosized copper catalyst precursor, and foam control agents in contact with alcohol vapor. The number and type of impellers in the reactor are selected to afford effective solids suspension, gas dispersion and mass transfer of alcohol to the copper-activated silicon. The reactor may have a single nozzle or multiple nozzles for the introduction of gaseous alcohol. A means of continuous or intermittent addition of activated nanosized copper catalyst precursor-silicon mixture, or of silicon, is also provided. Means for continuous removal and recovery of the volatile reaction products and unreacted alcohol are also desirably provided. Separation and purification of the trialkoxysilane products are performed utilizing methods known to those of skill in the art.

When the initial loading of silicon and nanosized copper catalyst precursor is activated according to the process of the present invention, continuous slurry phase Direct Synthesis of trialkoxysilanes is advantageously continued by adding only silicon, or silicon containing less nanosized copper catalyst precursor than that initially added. In this way, the copper concentration of the slurry is controlled to minimize the transformation of the alcohol to hydrocarbons and water (Equations 3 and 5 above). Disadvantages caused by water have been recited hereinabove.

The reaction is generally conducted at temperatures above about 150° C., yet below such a temperature as would degrade or decompose the reactants, solvents or desired products. Preferably, the reaction temperature is maintained in a range from about 200 to about 260° C. The reaction of methanol with the copper-activated silicon of the present invention is preferably performed at about 220 to 250° C., whereas the reaction of ethanol is preferably operated at about 200 to 240° C. A most preferred reaction temperature when using ethanol is about 200 to 210° C. as it prevents ethanol degradation which undesirably forms acetaldehyde and acetal, allows maintenance of high selectivity to triethoxysilane, and minimizes formation of the tetraethoxysilane.

The pressure at which the reaction is conducted may be varied from subatmospheric to superatmospheric. Atmospheric pressure is generally employed.

Preferably, the contents of the reaction mixture are agitated to maintain a well-mixed slurry of the copper-activated silicon particles and gaseous alcohol in the solvent. The exit line carrying the gaseous reaction mixture from the reactor is preferably well insulated to insure that the trialkoxysilane does not reflux. Refluxing may encourage the consecutive reaction of the trialkoxysilane with the alcohol resulting in loss of the desired trialkoxysilane product by the formation of the tetraalkoxysilane.

The presence of gaseous alcohol, hydrogen gas and other gases in the reactor may occasionally lead to foaming. This is undesirable since it may result in loss of solvent and copper-activated silicon from the reactor. The addition of foam control agents, preferably silicon-containing foam control agents such as SAG® 1000, SAG® 100, SAG® 47, available from OSi Specialties/Crompton Corporation, Greenwich, Conn., and FS 1265 from Dow Corning, Midland, Mich., will negate or control this problem. SAG® 1000, SAG® 100, SAG® 47 are compositions comprising polydimethylsilicones and silica. FS 1265 contains fluorinated silicones, for example, poly(dimethylsiloxane-co-trifluoropropylmethylsiloxanes). The foam control agent must be durable such that a single addition at the outset of a batch reaction is sufficient to avoid or mitigate foam formation until all of the silicon has been consumed.

At constant temperature, the reaction rate depends critically on the surface area and particle size of the silicon, and on the feed rate of the alcohol. Higher reaction rates are obtained at higher surface areas, finer particle sizes and higher alcohol feed rates. These parameters are selected so that a safe, economically sustainable product output is realized without endangerment to people, property and the environment.

High selectivity to trialkoxysilanes, high reaction rates and stable performance are realized when nanosized copper catalyst precursors are used in the invention. This is particularly so when nanosized copper and nanosized copper (I) oxide prepared by reductive decomposition of high surface area copper (II) hydroxide in alkylated benzenes or cyclopariffins is employed as the catalyst precursor. A unique feature of the trimethoxysilane Direct Synthesis of the present invention with nanosized copper catalyst precursors is a very high value of the overall product selectivity at the outset of the reaction, greater than 30. The selectivity declines to a stable value, greater than about 10, during the course of the reaction. This profile is in marked contrast to the Direct Synthesis as taught in the prior art in which product selectivity starts at low selectivity values, less than 10, and increases to stable values later in the reaction. Up to and higher than 50% silicon conversion, the process of the present invention produces more of the desired trimethoxysilane than the state-of-the-art technology. This is especially advantageous not only for continuous operation, but also for batch operation, wherein additional silicon is added to the reactor during the steady-state part of the synthesis.

A schematic drawing of a reactor and its ancillary equipment is shown in FIG. 1. Alcohol is delivered from the reservoir (1) via pump. (2), flow meter (3) and vaporizer (4) to reactor (5). Separate coils for alcohol and the recycle stream are contained within the vaporizer. The reactor contains silicon and nanosized copper catalyst precursor and/or copper-activated silicon suspended and dispersed in a high boiling, thermally stable solvent. A foam control agent is optionally present. Provision is made for nitrogen injection upstream of the vaporizer as shown in FIG. 1. Alcohol reacts with the copper-activated silicon in the reactor. The reactor is fitted with a hopper (6) for solids addition, an agitator (7) with one or more impellers, a heater and temperature controller (8), thermocouple bundle (9), internal baffles (10), spargers (11), pressure gauge (12) and pressure release safety valve (13). The gaseous reaction mixture leaves the reactor via the entrainment separator (14). Valve (15) permits sampling of the reaction mixture. An assembly of distillation columns (16) is provided for the separation of unreacted alcohol and lower boilers, also known as the lights, from the desired trialkoxysilane. The columns are connected to a reboiler (17) and reflux condenser (18). Liquid reaction product (19) containing the desired trialkoxysilane and byproducts with higher boiling points, known as heavies, are discharged from the unit to storage containers via pump (20). The temperatures of the columns and reboiler are controlled such that stream (21) contains the byproduct gases, unreacted alcohol, alkoxysilanes and azeotropes boiling lower than the desired trialkoxysilane also known as the lights. A portion (22) of the liquid overhead stream is returned to the distillation columns as reflux flow. The remainder (23) is recycled through the vaporizer and reinjected into the reactor so that the alcohol contained therein may be reacted with copper-activated silicon. The vent gas stream (24) is admitted into a flowmeter capable of measuring total gas flow.

EXAMPLES

The following Examples illustrate the preferred embodiments of the invention. These are not intended to limit the scope of the invention. Rather, they are presented merely to facilitate the practice of the invention by those of ordinary skill in the art.

TABLE I

Abbreviations and Units Used

| ABBREVIATION | MEANING |
|---|---|
| TMS | $HSi(OCH_3)_3$ |
| TMOS | $Si(OCH_3)_4$ |
| MeOH | $CH_3OH$ |
| TES | $HSi(OC_2H_5)_3$ |
| TEOS | $Si(OC_2H_5)_4$ |
| SEL | $HSi(OR)_3/Si(OR)_4$ |
| % Si/hr | Percent silicon converted per hour |
| N600L | NALKYLENE ® 600L |
| N550BL | NALKYLENE ® 550BL |
| TH59 | THERMINOL ® 59 |
| g | gram |
| kg | kilogram |
| L | liters |
| nm | nanometer |
| μm | micron |
| $m^2/g$ | square meters per gram |
| rpm | revolutions per minute |
| wt. % | weight percent |
| min | minute |
| s | second |

Equipment Used

Stainless Steel Slurry Reactor

A 5.8 liter reactor manufactured by Chemineer Inc., Dayton, Ohio, was used for some of the illustrative Examples presented herein. Four (4) 90° spaced, 1.27 cm wide baffles were affixed to the wall of the reactor. Agitation was provided by two impellers attached to an axial shaft. The bottom one was a six-blade Rushton turbine, 6.35 cm in diameter. A three-blade marine propeller of the same diameter was placed 10 cm above the turbine. A variable speed air-driven motor, whose rotational speed was measured by a magnetic tachometer, supplied power for agitation. An electric heating mantle controlled by a heater/temperature controller was used to heat the reactor.

Methanol or ethanol was supplied to the reactor from a 1 L storage container via a calibrated FMI laboratory pump. Coiled stainless steel tubing, 0.32 cm internal diameter×305 cm length, placed in a 4 L silicone oil bath controlled at 150° C. served as the alcohol vaporizer. A similar vaporizer coil was available for the recycle stream, but it was not used during the course of these experiments. The alcohol inlet line entered through the top of the reactor. It was heat traced to prevent condensation of the vapor. Alcohol vapor was injected 2.5 cm from the bottom of the reactor and below the level of the six-blade turbine through a single downward pointing (0.63 cm internal diameter) sparger. A pressure gauge attached the alcohol vapor inlet line gave higher readings (up to about 2 atmospheres) when the sparger was plugged. Ordinarily, the gauge was at zero. Additional alcohol was supplied to the storage container during an experiment to maintain an uninterrupted flow of this reagent.

Reaction products and unreacted alcohol exited the reactor through a 91.4 cm×2.54 cm internal diameter packed tube, which served as entrainment separator and partial distillation column to remove solvent and higher boiling silicates from the product stream. The packing was ceramic saddles and stainless steel mesh. Five thermocouples were distributed along the length of the tube to record temperatures and indicate foaming. The lowest thermocouple was flush with the top of the reactor. As was indicated hereinabove, foaming was controlled by the use of FS 1265 and SAG® 100. Flexible tubing connected the outlet of the entrainment separator/partial distillation column to the four-way valve (reference no. 15 in FIG. 1).

Two ten plate Oldershaw distillation columns served to separate the liquid reaction products and unreacted alcohol from the gases. Effluent from the reactor was admitted into the top trays of the lower column, which was attached to a 3 neck 2 L round bottom flask supported in a heating mantle. The upper column was capped by a magnetically controlled reflux condenser and distillation head with thermocouple. The reflux condenser and another condenser downstream were cooled to −25° C. by circulating silicone oil. Uncondensed gases exited the condenser through a vapor lock bubbler into the vent line. Wider tubing was employed downstream of the bubbler to avoid back pressures likely to shatter the glassware (columns, condensers and bubbler) or cause leaks at the joints. A gas sampling port was provided at a T joint downstream of the bubbler. Effluent gas flow was diluted with nitrogen prior to its discharge into the laboratory hood. A thermocouple was located in the second opening of the three-neck flask and the intake to an FMI laboratory pump in the other. The pump was used to transfer liquid product from the flask to Teflon coated polyethylene storage bottles. All glass containers used to store or sample trimethoxysilane and triethoxysilane were washed with dilute HCl, rinsed thoroughly with methanol (or ethanol) and oven dried at 110° C. prior to use.

Glass Slurry Reactor

A 2.0 liter glass reactor was also used to illustrate the process of the present invention. Agitation was provided by two pitched, glass blades attached to an axial shaft also of glass. The bottom blade was 5.7 cm in diameter and the top 3.9 cm. The blades were separated by 3.8 cm. A Model BDC 1850 Stirrer from Caframo Limited, Ontario, Canada, with digital speed control was the power source for agitation. An electric heating mantle controlled by a digital heater/temperature was used to heat the reactor.

Methanol or ethanol was supplied to the reactor from a 1 L calibrated addition funnel via a calibrated FMI pump. The alcohol was vaporized at about 130 to 160° C. by transit through a 30 cm long×0.32 cm diameter coiled, stainless steel tube placed in a silicone oil bath. Stainless steel tubing from the oil bath to the reactor inlet was also controlled at about 130 to about 160° C. with electrical heating tape. Reaction products and unreacted alcohol exited the reactor through a 40 cm long×2.5 cm diameter Vigreux column controlled at about 100° C. This served as an entrainment separator for solvent droplets. The gaseous reaction mixture was then admitted to a condenser, cooled to about 0° C. with chilled silicone oil, before it was collected in a sampling flask attached to a dry ice-isopropanol cold finger. Gas leaving the collection flask was cooled in a second dry ice-isopropanol cold finger before being vented to the hood through a vapor lock bubbler. The bubbler contained silicone oil and had an extra opening for the release of over-pressure.

Gas chromatographic analysis of the reaction product was performed as described below.

General Activation And Reaction Procedure

Typically, the reactor was charged with solvent, silicon, copper catalyst precursor, and foam control agent then sealed. The solvent to silicon ratio was typically 2:1 or 4:1. The slurry was agitated at about 900 rpm with nitrogen introduced during heating to the desired reaction temperature. Simultaneously, the alcohol vaporizer and feed inlet were heated to about 150 to about 170° C. and the refrigerant circulated through the reflux condenser was cooled to about −25° C. Alcohol flow to the reactor was initiated when all the set temperatures were attained.

Once the alcohol flow was underway, sampling and analysis of the vent gas stream (reference no. 24 in FIG. 1) for hydrogen were done every 10 to 30 minutes until a stable composition was established indicating the end of the induction period. Thereafter, gas sampling was done every 30 minutes to monitor hydrogen, hydrocarbons and ethers. During the course of the reaction, total vent gas flow was used as an approximate measure of the reaction rate according to the stoichiometry of Equation 1.

Samples were collected in previously acid washed, alcohol rinsed, oven-dried containers attached at the four-way sampling valve (reference no. 15 in FIG. 1) for about 2 to about 5 minutes every half hour. The containers were cooled in dry-ice during sample collection. Samples were weighed and analyzed by gas chromatography. The bulk of the liquid product was condensed in the three-neck flask, which served as the reboiler (reference no. 17 in FIG. 1) and transferred to storage. All of the data was used to calculate the temporal composition of the product stream, its selectivity to trialkoxysilane, the reaction rate and overall silicon conversion. Usually, reactions were terminated after more than 85% of the silicon charged to the reactor had been reacted. In some cases, terminations were made at lower and higher silicon conversions depending on the objective of the experiment.

Gas samples were analyzed for hydrogen, nitrogen and hydrocarbon (e.g. methane, ethane) content on a Hewlett Packard 5840 gas chromatograph fitted with a GS-Molesieve 30 m×0.53 mm internal diameter, available from J & W Scientific, Folsom, Calif., capillary column and flame ionization detector. Argon was the carrier gas. Gas chromatography-mass spectrometry was used to analyze for dimethyl ether. Liquid samples containing alkoxysilanes were analyzed on a Hewlett Packard 5890 gas chromatograph fitted with a 3.66 m×3.18 mm internal diameter stainless steel 20% OV-101 on 60/80 mesh Chromosorb WHP column, available from Supelco, Inc., Bellefonte, Pa., and thermal conductivity detector. Helium was the carrier gas. Data are reported in the Examples below only for the principal products, $HSi(OR)_3$ and $Si(OR)_4$ wherein R is methyl or ethyl). Byproducts such as $RSiH(OR)_2$ and $RSi(OR)_3$ were also formed, but at low concentrations.

Materials Used

Technical grade silicon samples utilized in the experiments of the illustrative Examples are identified in Table II along with relevant analytical data. In each case, particles in the size range, 45 to 300 μm, accounted for approximately 70 wt. % of the silicon. NALKYLENE® 550BL, NALKYLENE® 500, THERMINOL® 59, ISORCHEM® 113, SIRENE® X12L and WITCO® CARNATION® 70 were the solvents used. FS 1265 and SAG® 100 were the foam control agents. KOCIDE® Cu(OH)$_2$ with 57 to 59 wt. % Cu, bulk density of 171 to 229 kg/m$^3$, and surface area of 30 to 40 m$^2$/g was used where indicated.

TABLE II

Composition Of Silicon Samples Used In Illustrative Examples

| ELEMENT | SAMPLE Si-I | SILGRAIN ® | SAMPLE Si-II |
|---|---|---|---|
| Al, wt. % | 0.2 | 0.26 | 0.08 |
| Ba, ppm | 13.4 | | <3 |
| Ca, ppm | 517 | 350 | 600 |
| Cr, ppm | 28.6 | 10 | 58.9 |
| Cu, ppm | 19.5 | | 34.8 |
| Fe, wt. % | 0.39 | 0.26 | 0.38 |
| Mg, ppm | 23.9 | | 8.8 |
| Mn, ppm | 125 | 20 | 90.4 |
| Ni, ppm | <10 | | 15.5 |
| P, ppm | 25 | | 26.8 |
| Pb, ppm | <10 | | <10 |
| Sn, ppm | <10 | | <10 |
| Ti, ppm | 312 | 220 | 299 |
| V, ppm | 20.5 | | 14.3 |
| Zn, ppm | 6.6 | | <5 |
| Zr, ppm | 100 | | 29 |

Examples 1A to 1D

Example 1A illustrates the shortened induction time, higher reaction rate and higher trimethoxysilane (TMS) yield in the Direct Synthesis when nanosized copper (I) oxide was used as the source of catalytic copper.

Copper (I) oxide with 30 to 60 nanometers particle size was produced by decomposing 7.03 g KOCIDE® copper (II) hydroxide, containing 58.49 wt. % Cu, in 268.2 g NALKYLENE® 550BL at 250° C. After the hydrocarbon had been pipetted away from the settled solid, THERMINOL® 59 was added to the copper (I) oxide and that suspension transferred to the CHEMINEER® reactor. Table III records the quantities of the raw materials and the reaction conditions employed. A comparative experiment (Example 1B) was performed according to the teachings of U.S. Pat. No. 4,727,173 with the same lot of KOCIDE® copper (II) hydroxide as the source of copper.

Two additional control reactions were performed under the same conditions with commercial Cu$_2$O purchased from Fisher Scientific Co. (Example 1C) and Aldrich Chemical Co. (Example 1D). The average particle size of these solids was 10 μm (range 3 to 20 μm). Reactions were continued for 4 hours, but there was only a trace of HSi(OCH$_3$)$_3$ or H$_2$ formation in each experiment.

TABLE III

Improvements In Reactivity Of Direct Synthesis Of TMS With Use Of Nanosized Cu$_2$O

| PARAMETER | EXAMPLE 1A | EXAMPLE 1B (CONTROL) |
|---|---|---|
| KOCIDE ® Cu(OH)$_2$, g | 7.03 | 7.05 |
| Cu Concentration, ppm | 3859 | 4122 |
| THERMINO ® 59, g | 2082.0 | 2093.7 |
| FS1265, g | 0.9 | 1.0 |
| Silicon (Si-I), g | 1000.0 | 1000.3 |
| Temperature, ° C. | 245.2 ± 2.5 | 245.5 ± 1.7 |
| Agitation Rate, rpm | 900 | 900 |
| Methanol Flow, g/min | 5.05 | 5.05 |
| Induction Time, hr | 2 | 6.8 |
| Maximum TMS, wt. % | 91.88 | 87.38 |
| Average Rate, % Si/hr | 6.89 | 6.13 |
| Silicon Conversion, % | 94.5 | 90.6 |
| TMS Yield, g | 3873.9 | 3755.7 |
| TMOS Yield, g | 221.8 | 196.7 |
| Selectivity | 17.46 | 19.09 |

In the experiment of Example 1A, HSi(OCH$_3$)$_3$ was 83.83 wt. % and silicon conversion was 11.54 wt. % two hours into the reaction. In contrast, the experiment of Example 1B required 6.8 hours to reach 83.30 wt. % HSi(OCH$_3$)$_3$ and the silicon conversion was then 31.84 wt. %. These differences are displayed in FIGS. 2A and 2B. In each experiment, the reaction was terminated at the crossover of the methanol and HSi(OCH$_3$)$_3$ curves. Crossover occurred in 14.78 hours at about 90% silicon conversion in Example 1B and in 13.72 hours at about 95% silicon conversion in Example 1A. Accordingly, both the reaction rate and the yield of HSi(OCH$_3$)$_3$ were higher in Example 1A wherein nanosized Cu$_2$O was used, than in the control, Example 1B. The copper concentration in both experiments (see Table III) was about 4000 ppm based on the weight of silicon charged to the reactor.

The crossover point was greater than 95% silicon conversion in other experiments similar to Example 1B. In one such experiment, induction time was 1.5 hours and crossover occurred at about 99% silicon conversion. The yield of HSi(OCH$_3$)$_3$ was 4.18 kg; reaction rate was 7.30% Si/hr.

Examples 2A to 2D

These Examples illustrate the Direct Synthesis of triethoxysilane with nanosized copper (1) oxide as the source of catalytic copper.

For the experiments of Examples 2A, 2C and 2D, KOCIDE® Cu(OH)$_2$ having 58.49 wt. % Cu, was decomposed to nanosized Cu$_2$O in NALKYLENE® 550BL at 250° C. for 1 hr. NALKYLENE® 500 was used in Example 2B. The weights of Cu(OH)$_2$ used are given in Table IV. Nanosized Cu$_2$O and the excess alkylated benzene solvent were added to the CHEMINEER® reactor along with the other raw materials as shown in the Table. Note that Direct Synthesis of triethoxysilane was done in NALKYLENE® 550BL for Examples 2A, 2C and 2D, and in NALKYLENE® 500 for Example 2B.

The reactions are compared at about 40% silicon conversion, since they were not all run to the same extent. The high activity of the nanosized Cu$_2$O is evident in Examples 2A and 2B. Average reaction rates were 6 to 6.5% Si/h at about 200° C. with the use of 500 to 750 ppm copper. Selectivity to triethoxysilane (TES) was also very good. Copper concentrations in the range 2000 to 4250 ppm (Examples 2C and 2D) afforded higher reaction rates without loss of selectivity to TES.

TABLE IV

Direct Synthesis Of TES With 515 to 4235 ppm Cu From Nanosized Cu$_2$O

| PARAMETER | Example 2A | Example 2B | Example 2C | Example 2D |
|---|---|---|---|---|
| KOCIDE® Cu(OH)$_2$, g | 0.500 | 0.714 | 2.000 | 4.100 |
| NALKYLENE®, g | 2022.6 | 2020.5 | 2008.2 | 2104.2 |
| FS1265, g | 1.5 | 3.14 | 1.5 | 1.5 |
| SAG® 47, g | 0.8 | 1.61 | 0.8 | |
| Silicon (Si-II), g | 567.6 | 566.7 | 569.2 | 566.2 |
| Cu Conc., ppm | 515 | 737 | 2055 | 4235 |
| Temperature, °C | 195.1 ± 0.9 | 202.3 ± 0.8 | 204.5 ± 7.3 | 218.9 ± 3.2 |
| Agitation Rate, rpm | 900 | 900 | 900 | 900 |
| Ethanol Flow, g/min | 10.1 | 10.1 | 10.1 | 10.1 |
| Average Rate, % Si/hr | 6.04 | 6.46 | 13.32 | 13.63 |
| Silicon Conversion, % | 39.28 | 40.67 | 39.95 | 39.93 |
| TES Yield, g | 1242.38 | 1323.83 | 1301.71 | 1289.12 |
| TEOS* Yield, g | 78.32 | 30.97 | 35.87 | 42.13 |
| Selectivity | 15.86 | 42.75 | 36.29 | 30.60 |

Example 3

This Example illustrates the Direct Synthesis of triethoxysilane with nanosized copper (II) oxide as the source of catalytic copper.

Nanosized CuO was prepared from 0.356 g KOCIDE® Cu(OH)$_2$ and 50.3 g decane. Most of the decane was decanted (about 32 g) and the catalyst precursor was added to the glass reactor along with 250.86 g silicon (Si-II), 1002 g NALKYLENE® 500, 3.29 g FS 1265 (300 cSt), and 1.42 g SAG® 47. The reaction mixture was stirred at 820 rpm and heated to 205° C. Ethanol was introduced to the vaporizer at 4.12 g/min. Reaction was continued for 7.92 hours before it was terminated.

In that time, 680.83 g TES and 23.85 g TEOS were produced. The selectivity to TES was 28.55. Silicon conversion reached 47.68% and the average rate was 6.02% Si/h. This outstanding performance was obtained with nanosized CuO, equivalent to 819 ppm Cu (based on amount of silicon charged).

Examples 4A to 4D

These Examples illustrate the use of mixtures of nanosized copper and nanosized copper oxides in the Direct Synthesis of trimethoxysilane.

The nanosized copper catalyst precursors were generated from KOCIDE® copper (II) hydroxide and the hydrocarbons listed in Table V. CARNATIONS 70 was retained in the catalyst precursor and added to the reactor in the experiment of Example 4B. The hydrocarbons were filtered from the catalyst precursors in Examples 4A and 4C, but decanted in Example 4D.

Direct Synthesis of trimethoxysilane was performed in the CHEMINEER® reactor with the quantities of raw materials and under the conditions shown in Table VI.

TABLE V

Nanosized Copper And Copper Oxides Used In Examples 4A to 4D

| EXAMPLE | HYDROCARBON | NANOPHASES | PARTICLE SIZE |
|---|---|---|---|
| 4A | CARNATION® 70 | Cu$_2$O major, CuO minor | 1 to 15 nm |
| 4B | CARNATION® 70 | Cu$_2$O major, CuO minor | 1 to 15 nm |
| 4C | ISORCHEM® 113 | Cu$_2$O major, CuO minor | 20 to 100 nm |
| 4D | SIRENE® X12L | Cu$_2$O major, Cu minor | 20 to 50 nm |

Since the reactions were not all run above 85% silicon conversion, the data comparisons in Table VI are shown for about 77% silicon conversion. Each Example exhibits short induction time, high reaction rate and very good selectivity to TMS. Thus, mixtures of nanosized copper oxides and nanosized copper are effective catalyst precursors for the Direct Synthesis of trimethoxysilane. Example 4B also illustrates that mixtures of THERMINOL® 59 and CARNATIONS 70 are suitable solvents for the slurry-phase Direct Synthesis of trimethoxysilane with nanosized copper catalyst precursors.

TABLE VI

Use Of Nanosized Copper And Copper Oxides In The Direct Synthesis Of TMS

| PARAMETER | Example 4A | Example 4B | Example 4C | Example 4D |
|---|---|---|---|---|
| Total Cu, g | 4.131 | 4.188 | 4.073 | 4.073 |
| THERMINOL® 59, g | 2261.8 | 2033.8 | 2164.9 | 2117.5 |
| FS1265, g | 0.86 | 0.86 | 0.80 | 0.81 |
| Silicon (Si-I), g | 1062.4 | 1051.7 | 1080.5 | 1082.2 |
| Cu Conc., ppm | 3888 | 3982 | 3770 | 3764 |
| Temperature, °C | 255.1 ± 1.2 | 254.8 ± 2.4 | 253.7 ± 3.1 | 254.9 ± 1.7 |
| Agitation Rate, rpm | 900 | 900 | 900 | 900 |
| Methanol Flow, g/min | 4.99 | 4.99 | 4.99 | 4.99 |
| Induction Time, h | 2.25 | 1.95 | 1.60 | 1.22 |
| Maximum TMS, wt. % | 88.82 | 89.51 | 89.02 | 88.62 |
| Average Rate, % Si/h | 6.34 | 5.81 | 6.81 | 6.50 |
| Silicon Conversion, % | 77.17 | 78.57 | 77.07 | 76.70 |
| TMS Yield, g | 3361.97 | 3371.07 | 3361.53 | 3405.95 |
| TMOS* Yield, g | 160.04 | 162.85 | 196.86 | 146.88 |
| Selectivity | 21.01 | 20.70 | 17.08 | 23.19 |

Examples 5A to 5B

These Examples illustrate the improved reactivity, selectivity and silicon conversion obtained in the Direct Synthesis of trimethoxysilane when a nanosized copper catalyst precursor is used with acid leached silicon (SILGRAIN®)

Nanosized Cu$_2$O for Example 5A was prepared from 7.00 g KOCIDE® Cu(OH)$_2$. The same lot of KOCIDE® Cu(OH)$_2$ was used in the control experiment in Example 5B. The same lot of SILGRAIN® was also used in both experiments. Experimental data and results are summarized in Table VII and FIGS. 3A and 3B.

Figure 3A:
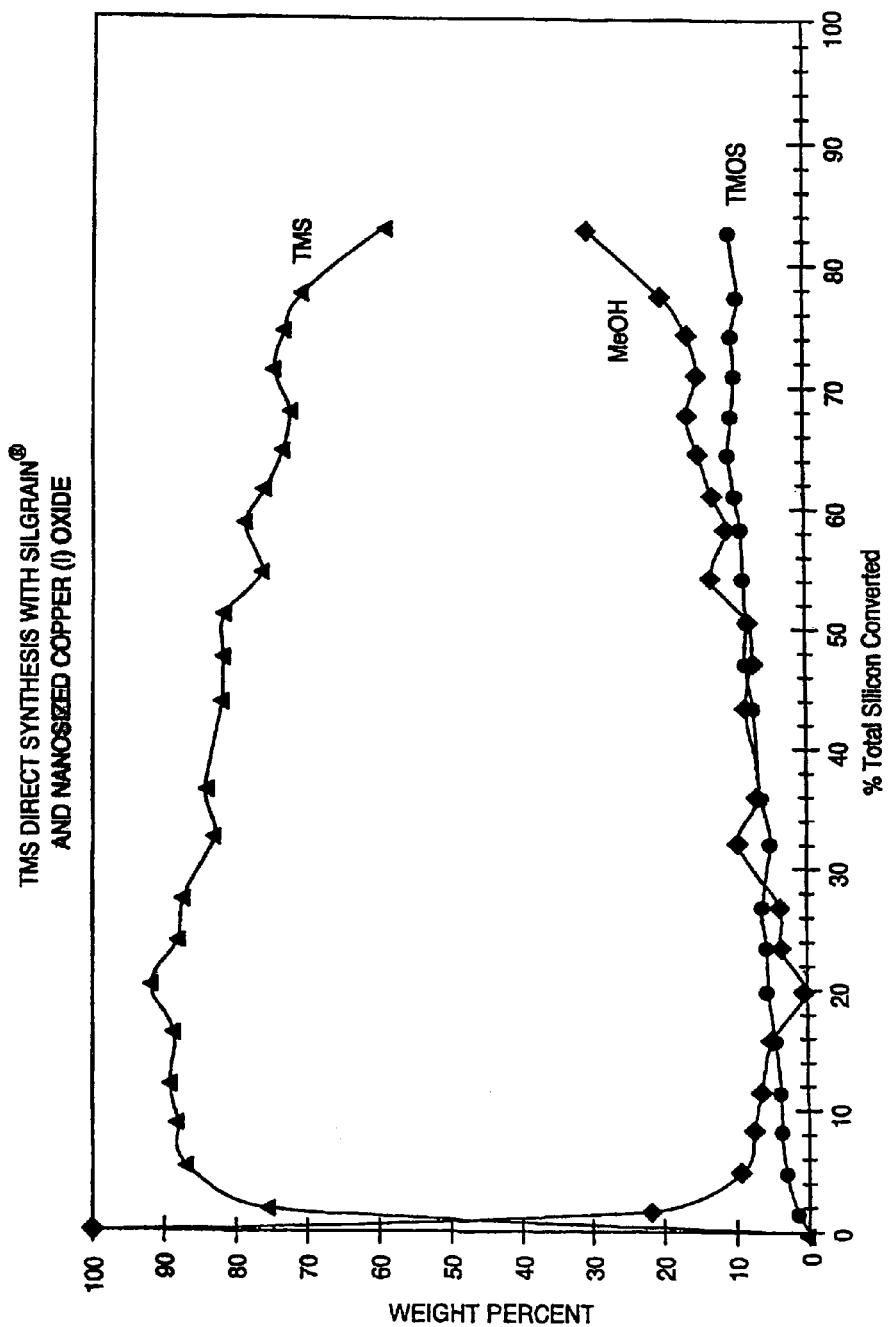
FIG. 3A is a plot of the composition of the reaction mixture during the Direct Synthesis of trimethoxysilane, HSi(OCH$_3$)$_3$ with SILGRAIN® and nanosized copper (I) oxide in accordance with the present invention.
Figure 3B:
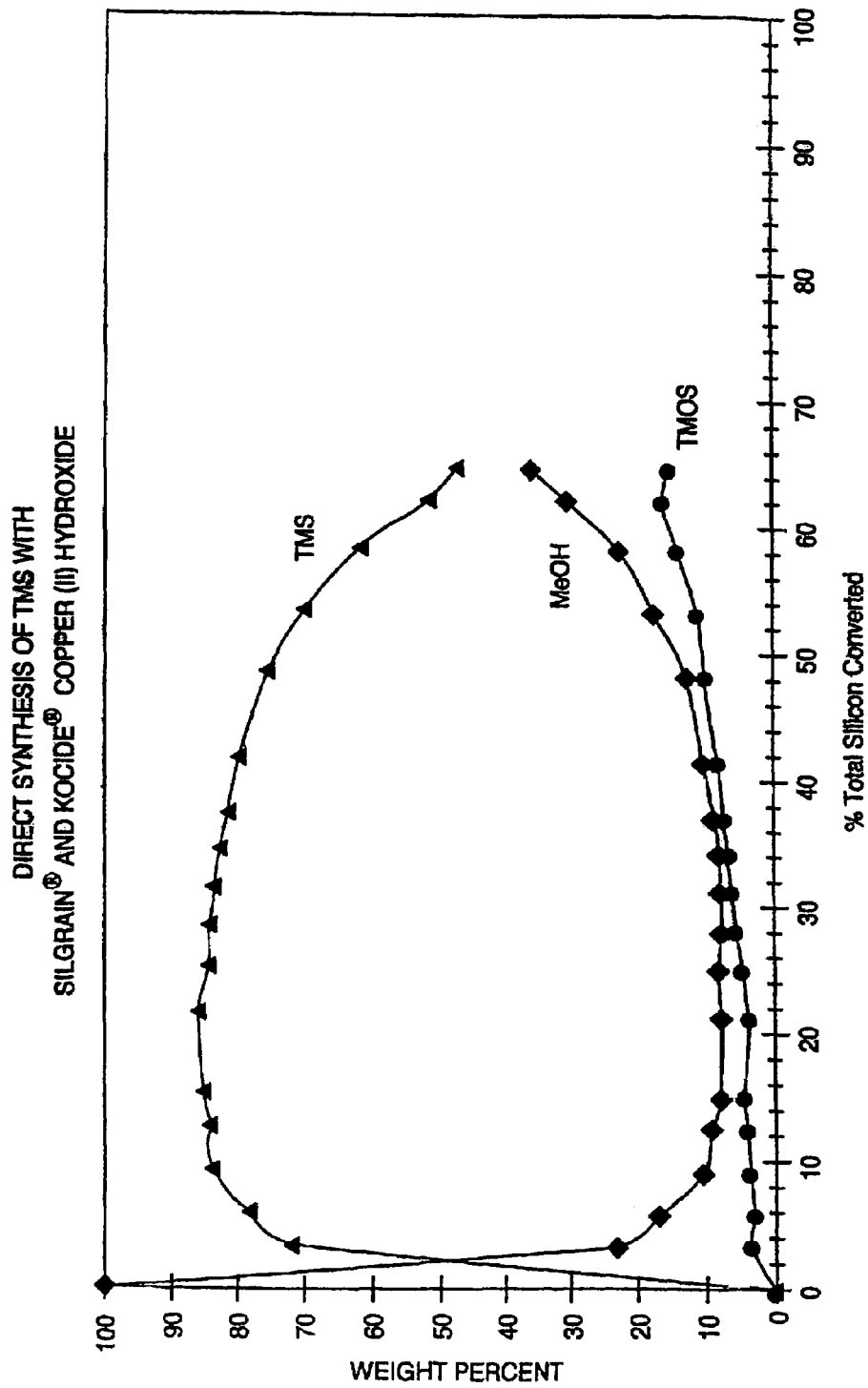
FIG. 3B is a plot of the composition of the reaction mixture during the Direct Synthesis of trimethoxysilane, HSi(OCH$_3$)$_3$ with SILGRAIN® and KOCIDE® copper (II) hydroxide having 57 to 59 wt. % copper.

FIG. 3A shows that the content of TMS in the reaction mixture of Example 5A was still greater than 50 wt. % at about 85% silicon conversion. In contrast, TMS content in the control reaction of SILGRAIN® (Example 5B and FIG. 3B) was less than 50 wt. % at about 65% silicon conversion. Thus, the use of nanosized $Cu_2O$ increases the stability of the Direct Synthesis of trimethoxysilane with SILGRAIN®. Table VII shows that reactivity and selectivity are also enhanced with the use of nanosized copper catalyst precursors. Values in parentheses in Example 5A column are for 64.62% silicon conversion, which is approximately the point at which the control reaction was terminated. Note that the higher TMS yield at about 65% in Example 5B results from the larger quantity of silicon charged in that experiment.

TABLE VII

Improvements In Direct Synthesis Of TMS From SILGRAIN ® With The Use Of Nanosized Copper (I) Oxide

| PARAMETER | EXAMPLE 5A | EXAMPLE 5B (CONTROL) |
|---|---|---|
| Cu Concentration, ppm | 3829 | 3547 |
| THERMINOL ® 59, g | 2170.0 | 2036.4 |
| FS1265, g | 0.75 | 0.85 |
| SILGRAIN ®, g | 1048.9 | 1187.3 |
| Temperature, ° C. | 251.7 ± 1.5 | 254.0 ± 2.1 |
| Agitation Rate, rpm | 900 | 900 |
| Methanol Flow, g/min | 4.99 | 4.99 |
| Induction Time, hr | 1.00 | 1.70 |
| Maximum TMS, wt. % | 91.68 | 86.22 |
| Average Rate, % Si/hr | 6.59 (6.91)* | 5.82 |
| Silicon Conversion, % | 85.11 (64.62)* | 64.79 |
| TMS Yield, g | 3538.82 (2709.81)* | 3010.24 |
| TMOS Yield, g | 324.65 (203.00)* | 326.44 |
| Selectivity | 10.90 (13.35)* | 9.22 |

*Values in parentheses are for comparison with the control at approximately the same silicon conversion.

Examples 6A to 6B

This Example illustrates the use of nanosized copper (I) chloride in the Direct Synthesis of triethoxysilane. Nanosized CuCl was prepared from nanosized $Cu_2O$ and HCl gas. The glass reactor was charged with 1100 g NALKYLENE® 500, 551.4 g silicon (Si—II), 1.0 g nanosized CuCl, 1.5 g FS1265 (300 cSt), and 1.5 g FS1265 (1000 cSt). This mixture was stirred at 816 rpm, heated to 220° C. and maintained at that temperature for 2 hours prior to the introduction of ethanol. The ethanol feed rate was 5.44 g/min.

After three hours, the reaction had produced 461.36 g TES and 18.94 g TEOS. The selectivity was 24.36.

Examples 7A to 7C

These Examples illustrate the Direct Synthesis of trimethoxysilane when the nanosized copper catalyst precursor was prepared according to U.S. Pat. No. 4,539,041 to Figlarz, et al.

Three precursors were synthesized. The quantities of KOCIDE® $Cu(OH)_2$, and ethylene glycol used in the preparations are set forth in Table VIII. The molar ratio, [Cu/$HOC_2H_4OH$], was varied to change the Cu/$Cu_2O$ balance and the particle size in the product. According to Figlarz, et al., increasing $HOC_2H_4OH$ results in smaller particle size and more reduction to elemental copper. However, our data are contrary (see Table VIII). $Cu_2O$ was more prevalent at lower [Cu/$HOC_2H_4OH$] molar ratios. Our $Cu_2O$ exhibited broad x-ray diffraction peaks indicative of small particle sizes in the submicron and nanometer range.

TABLE VIII

Copper And Copper Oxides Made By The "Polyol Process" Of U.S. Pat. No. 4,539,041

| EXAMPLE | REAGENTS & CONDITIONS | [Cu/$HOC_2H_4OH$] MOLAR RATIO | PHASES AND PARTICLE SIZE |
|---|---|---|---|
| 7A | 12.1 g $Cu(OH)_2$ & 204.5 g $HOC_2H_4OH$, 198° C./1.5 h | 0.034 | $Cu_2O$ |
| 7B | 11.9 g $Cu(OH)_2$ & 100 g $HOC_2H_4OH$, 198° C./1.5 h | 0.068 | $Cu_2O$ |
| 7C | 51 g $Cu(OH)_2$ & 349 g $HOC_2H_4OH$, 198° C./1.5 h | 0.083 | Cu with trace of $Cu_2O$; 150 nm to 1.5 µm |

Direct Synthesis was performed in the CHEMINEER® reactor with about 2 kg THERMINOL® 59, about 1 kg silicon (Si-I), 1 g FS1265 and copper concentration of about 4000 ppm. The reaction was terminated after 11.25 hours (55.85% Si conversion) in Example 7C, but was continued to 14.55 hours (82.85% Si conversion) and 18.2 hours (91.11% Si conversion), respectively, in Examples 7B and 7A. The yield of TMS was 3.7 kg in Example 7A, 3.3 kg in Example 7B and 2.3 kg in Example 7C.

Commercial copper and copper oxides with particles in the micron range are not effective catalyst precursors for the Direct Synthesis of trimethoxysilane (see Examples 1C and 1D above). However, the data of Examples 7A to 7C establish that the copper and copper oxides made by the "polyol process" effectively catalyze the Direct Synthesis at copper concentrations as low as 4000 ppm.

Examples 8A to 8B

These Examples illustrate the unique selectivity profile typically observed during the Direct Synthesis of trimethoxysilane when nanosized copper (I) oxide is the source of catalytic copper.

Two experiments are presented in this Example. Example 8A was run in a similar manner as Example 1A. The nanosized copper (I) oxide was prepared by the thermal decomposition of KOCIDE® $Cu(OH)_2$ (57.37 wt % Cu) in NALKYLENE® 550BL. The same lot of KOCIDE® $Cu(OH)_2$ was used in the control experiment, Example 8B. Table IX is a summary of the experimental data. FIG. 4 presents a comparison of the product selectivity versus silicon conversion for both experiments. The selectivity values shown are cumulative data for all of the product made up to that point in the reaction.

TABLE IX

Raw Materials, Conditions And Results Of The Experiments of Examples 8A and 8B

| PARAMETER | EXAMPLE 8A | EXAMPLE 8B (CONTROL) |
|---|---|---|
| Cu Concentration, ppm | 3999 | 4028 |
| THERMINOL ® 59, g | 2105.3 | 2122.9 |
| FS1265, g | 0.65 | 0.68 |
| Silicon (Si-I), g | 1047.3 | 1042.5 |
| Temperature, ° C. | 252.2 ± 2.1 | 251.7 ± 1.8 |
| Agitation Rate, rpm | 900 | 900 |
| Methanol Flow, g/min | 5.54 | 5.54 |
| Induction Time, hr | 1.5 | 3.15 |
| TMS Yield, g | 4180.90 | 4159.58 |

FIG. 4 shows that the experiment of Example 8A was very selective (SEL greater than 30) at the outset. Product selectivity declined thereafter and was about 14 at the end of the reaction. In contrast, product selectivity was less than 5 at the beginning of the experiment of Example 8B. It increased to about 15 by the end of the reaction. The two curves are approximately equal after 70% silicon conversion. More of the desirable product, HSi(OCH$_3$)$_3$, is made in Example 8A, particularly at up to about 50% silicon conversion. This difference in product selectivity profiles presents an advantage when nanosized copper catalyst precursors are used in continuous reactions and in semi-continuous, batch reactions in which more than one silicon charge is used with a single load of solvent. The addition of silicon, nanosized copper oxide and/or silicon activated with a nanosized copper source to the reactor is made during the course of the reaction to keep the selectivity higher than it would be for a batch reaction with a conventional copper catalyst precursor. In the examples given here, the additional solids are introduced prior to 70% silicon conversion, and preferably between 20 to 50% silicon conversion so that product selectivity may be maintained at greater than 20.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A process for the direct synthesis of trialkoxysilanes comprising the steps of:
    (a) providing a slurry of silicon metal, and a copper catalyst precursor having an average particle size of about 0.1 to 60 nanometers in a thermally stable solvent;
    (b) forming a copper-silicon intermetallic;
    (c) reacting said copper-silicon intermetallic with an alcohol of formula ROH wherein R is an alkyl group having 1 to 6 carbon atoms inclusive, to form a trialkoxysilane of the formula HSi(OR)$_3$ wherein R is as previously defined;
    (d) recovering the trialkoxysilane; and
    (e) remediating the thermally stable solvent for subsequent Direct Synthesis of trialkoxysilanes.

2. The process of claim 1 wherein in step (a) said slurry is formed with nanosized silicon metal.

3. The process of claim 1 wherein in step (a) said silicon metal is produced by acid leaching and said copper catalyst precursor comprises nanosized copper chloride.

4. The process of claim 1 wherein in step (a), said thermally stable solvent is a member selected from the group consisting of linear and branched paraffins, cycloparaffins, alkylated benzenes, aromatic ethers, and polyaromatic hydrocarbons.

5. The process of claim 1 wherein in step (a), an initial copper concentration is about 300 to about 5000 ppm based on an amount of said silicon metal.

6. The process of claim 1 wherein in step (a), said copper catalyst precursor is selected from the group consisting of nanosized copper, nanosized copper oxides, nanosized copper chlorides, other nanosized copper salts, and mixtures thereof.

7. The process of claim 1 wherein in step (b) said copper-silicon intermetallic is formed by heating said copper catalyst precursor in said slurry for about 0.01 to about 24 hours at a temperature of about 20 to about 400° C.

8. The process of claim 1 wherein in step (b) said copper-silicon intermetallic is formed in situ.

9. The process of claim 1 wherein in step (b) said copper-silicon intermetallic is formed in a separate reaction vessel prior to reaction with said alcohol.

10. The process of claim 1 wherein in step (c) said alcohol is introduced as a gaseous stream to react with said copper-silicon intermetallic.

11. The process of claim 1 wherein in step (c) more than one alcohol is present to react with said copper-silicon intermetallic.

12. The process of claim 1 wherein step (c) comprises reacting said copper-silicon intermetallic with ethanol at a temperature of about 200 to about 210° C.

* * * * *